United States Patent
Li et al.

(10) Patent No.: US 7,026,175 B2
(45) Date of Patent: Apr. 11, 2006

(54) HIGH THROUGHPUT MEASUREMENT OF VIA DEFECTS IN INTERCONNECTS

(75) Inventors: Jiping Li, Fremont, CA (US); Peter G. Borden, San Mateo, CA (US); Edgar B. Genio, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/813,407

(22) Filed: Mar. 29, 2004

(65) Prior Publication Data
US 2005/0214956 A1    Sep. 29, 2005

(51) Int. Cl.
*H01L 21/66* (2006.01)
(52) U.S. Cl. .............................. 438/14; 438/16; 438/17
(58) Field of Classification Search ................. 438/14, 438/16, 17, 7
See application file for complete search history.

(56) References Cited

U.S. PATENT DOCUMENTS

| | | | |
|---|---|---|---|
| 3,462,602 A | 8/1969 | Apple | 250/83 |
| 3,803,413 A | 4/1974 | Vanzetti et al. | 250/338 |
| 3,909,602 A | 9/1975 | Micka | 716/4 |
| 4,201,087 A | 5/1980 | Akita et al. | 73/339 |
| 4,255,971 A | 3/1981 | Rosencwaig | 73/606 |
| 4,455,741 A | 6/1984 | Kolodner | 29/574 |
| 4,466,748 A | 8/1984 | Needham | 374/129 |
| 4,521,118 A | 6/1985 | Rosencwaig | 374/5 |
| 4,522,510 A | 6/1985 | Rosencwaig | 374/7 |
| 4,579,463 A | 4/1986 | Rosencwaig et al. | 374/57 |
| 4,632,561 A | 12/1986 | Rosencwaig et al. | 356/432 |
| 4,634,290 A | 1/1987 | Rosencwaig | 374/5 |
| 4,636,088 A | 1/1987 | Rosencwaig et al. | 374/5 |
| 4,679,946 A | 7/1987 | Rosencwaig et al. | 374/5 |
| 4,750,822 A | 6/1988 | Rosencwaig et al. | 324/445 |
| 4,795,260 A | 1/1989 | Schuur et al. | 356/400 |
| 4,873,434 A | 10/1989 | See et al. | 250/235 |
| 4,950,990 A | 8/1990 | Moulder | 324/224 |
| 5,042,951 A | 8/1991 | Gold et al. | 356/369 |
| 5,074,669 A | 12/1991 | Opsal | 356/447 |
| 5,128,864 A | 7/1992 | Waggener et al. | 364/413 |
| 5,149,978 A | 9/1992 | Opsal et al. | 250/234 |

(Continued)

FOREIGN PATENT DOCUMENTS

EP    0 718 595    12/1995

(Continued)

OTHER PUBLICATIONS

Paquin, "Properties of Metals", Handbook of Optics, vol. II, McGraw-Hill, Inc. (month unavailable), 1995, pp. 35.3-35.7.

(Continued)

*Primary Examiner*—Michael Trinh
(74) *Attorney, Agent, or Firm*—Omkar Suryadevara

(57) ABSTRACT

Heat is applied to a conductive structure that includes one or more vias, and the temperature at or near the point of heat application is measured. The measured temperature indicates the integrity or the defectiveness of various features (e.g. vias and/or traces) in the conductive structure, near the point of heat application. Specifically, a higher temperature measurement (as compared to a measurement in a reference structure) indicates a reduced heat transfer from the point of heat application, and therefore indicates a defect. The reference structure can be in the same die as the conductive structure (e.g. to provide a baseline) or outside the die but in the same wafer (e.g. in a test structure) or outside the wafer (e.g. in a reference wafer), depending on the embodiment.

17 Claims, 21 Drawing Sheets

U.S. PATENT DOCUMENTS

| | | | |
|---|---|---|---|
| 5,159,412 A | 10/1992 | Willenborg et al. | 356/445 |
| 5,181,080 A | 1/1993 | Fanton et al. | 356/381 |
| 5,228,776 A | 7/1993 | Smith et al. | 374/5 |
| 5,304,931 A | 4/1994 | Flamig et al. | 324/309 |
| 5,377,006 A | 12/1994 | Nakata | 356/349 |
| 5,574,562 A | 11/1996 | Fishman et al. | 356/432 |
| 5,790,251 A | 8/1998 | Hagiwara | 356/351 |
| 5,877,860 A | 3/1999 | Borden | 356/376 |
| 5,883,518 A | 3/1999 | Borden | 324/752 |
| 5,966,019 A | 10/1999 | Borden | 324/752 |
| 5,978,074 A | 11/1999 | Opsal et al. | 356/72 |
| 6,040,936 A | 3/2000 | Kim et al. | 359/245 |
| 6,049,220 A | 4/2000 | Borden et al. | 324/765 |
| 6,054,868 A | 4/2000 | Borden et al. | 324/752 |
| 6,154,280 A | 11/2000 | Borden | 356/376 |
| 6,169,601 B1 | 1/2001 | Eremin et al. | 356/240 |
| 6,178,020 B1 | 1/2001 | Schultz et al. | 359/107 |
| 6,268,916 B1 | 7/2001 | Lee et al. | 356/432 |
| 6,281,027 B1 | 8/2001 | Wei et al. | 438/14 |
| 6,323,951 B1 | 11/2001 | Borden et al. | 356/502 |
| 6,327,035 B1 | 12/2001 | Li et al. | 356/432 |
| 6,330,361 B1 | 12/2001 | Mitchell et al. | 382/211 |
| 6,387,715 B1 | 5/2002 | David et al. | 438/16 |
| 6,400,454 B1 | 6/2002 | Noguchi et al. | 356/237 |
| 6,426,644 B1 | 7/2002 | Borden et al. | 324/765 |
| 6,483,594 B1 | 11/2002 | Borden et al. | 356/502 |
| 6,489,801 B1 | 12/2002 | Borden et al. | 324/766 |
| 6,528,333 B1 | 3/2003 | Jun et al. | 438/16 |
| 6,541,747 B1 | 4/2003 | Kikuchi et al. | 250/201 |
| 6,559,942 B1 | 5/2003 | Sui et al. | 356/369 |
| 6,694,284 B1 | 2/2004 | Nikoonahad et al. | 702/155 |
| 6,720,248 B1 | 4/2004 | Ryo | 438/622 |
| 6,747,355 B1 | 6/2004 | Abiru | 257/758 |
| 6,812,047 B1 | 11/2004 | Borden et al. | 438/16 |
| 6,878,559 B1 * | 4/2005 | Borden et al. | 438/14 |
| 6,885,444 B1 * | 4/2005 | Borden et al. | 356/239.8 |
| 6,906,801 B1 * | 6/2005 | Borden et al. | 356/432 |
| 2001/0017878 A1 | 8/2001 | Nozoe et al. | 374/7 |
| 2002/0126732 A1 | 9/2002 | Shakouri et al. | 374/130 |
| 2002/0167326 A1 | 11/2002 | Borden et al. | 324/752 |
| 2003/0165178 A1 | 9/2003 | Borden et al. | 374/5 |

FOREIGN PATENT DOCUMENTS

| | | |
|---|---|---|
| JP | 405006929 A | 1/1993 |
| JP | 2000 009443 A | 1/2000 |
| WO | ISR PCT/US99/12999 | 9/1999 |
| WO | ISR PCT/US01/07475 | 7/2001 |
| WO | ISR PCT/US03/06239 | 2/2003 |
| WO | ISR PCT/US03/06379 | 2/2003 |

OTHER PUBLICATIONS

Rosencwaig et al. "Detection of Thermal Waves Through Optical Reflectance", Appl Phys. Lett. 46, Jun. 1985, pp1013-1015.

Rosencwaig, "Thermal-Wave Imaging", SCIENCE, vol. 218, No. 4569, Oct. 1982, pp. 223-228.

Opsal et al. "Thermal-Wave Detection and Thin-Film Thickness Measurements with Laser Beam Deflection", Applied Optics, vol. 22, No. 20, Oct. 1983, pp. 3169-3176.

Rosencwaig, "Thermal Wave Characterization and Inspection of Semiconductor Materials and Devices", Chapter 5 (pp. 97-135) of Photoacoustic and Thermal Wave Phenomena in Semiconductors, North Holland (month unavailable) 1987.

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, (month unavailable) 1990.

J. Kolzer et al "Thermal Imaging and Measurement Techniques for Electronic Materials and Devices" Microelectronic Engineering, vol. 31, 1996 (month unknown) pp. 251-270.

C. Martinsons et al. "Recent progress in the measurement of thermal properties of hard coatings" Thin Solid Films, vol. 317, Apr. 1998, 455-457.

S. Wolf and R. N. Tauber, "Silicon Processing For The VLSI Era", vol. 1, 1986, pp. 388-399.

Yaozhi Hu and Sing Pin Tay, "Spectroscopic ellipsometry investigation of nickel silicide formation by rapid thermal process", J. Vac. Sci. Technology, American Vacuum Soc. May/Jun. 1998, pp. 1820-1824.

Bristow, Thomas C. and Dag Lindquist, "Surface Measurements With A Non-Contact Nomarski-Profiling Instrument", Interferometric Metrology, SPIE vol. 816, Aug. 1987, pp. 106-110.

Charles Kittel, "Introduction to Solid State Physics", Fourth Edition, John Wiley & Sons, published prior to Mar. 1, 2002, pp. 262-264.

Rolf E. Hummel, "Electronic Properties of Materials, An Introduction For Engineers", published prior to Mar. 1, 2002, pp. 137-145.

H.S. Carslaw and J.C. Jaeger, "Conduction of Heat In Solids", Second Edition, published prior to Mar. 1, 2002, pp. 64-66.

A. Rosencwaig, "Thermal Wave Measurement of Thin-Film Thickness", 1986 American Chemical Society, pp. 182-191.

A. Rosencwaig et al., "Thin-Film Thickness Measurements with Thermal Waves", Journal De Physique, Oct. 1983, pp. C6-483-C6-489.

S. Ameri et al., "Photo-Displacement Imaging", Mar. 30, 1981, pp. 337-338.

L. Chen et al., "Thermal Wave Studies of Thin Metal Films Using the Meta-Probe-A New Generation Photothermal System" 25th Review of Progress in QNDE, Snowbird, UT Jul. 19-24, 1998, pp 1-12.

P. Alpern and S. Wurm, "Modulated Optical Reflectance Measurements on Bulk Metals and Thin Metallic Layers", J. Appl. Phys. 66(4), Aug. 15, 1989, pp 1676-1679.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp 120-131.

A. Rosenwaig, "Process Control In IC Manufacturing With Thermal Waves", Review of Progress in Quantitative Nondestructive Evaluation, vol. 9, 1990, pp 2031-2037.

K. Farnaam, "Measurement of Aluminum Alloy Grain Size on Product Wafers and its Correlation to Device Reliability", 1990 WLR Final Report, pp 97-106.

B.C. Forget et al., "High Resolution AC Temperature Field Imaging", Electronic Letters Sep. 25, 1997, vol. 33 No. 20, pp 1688-1689.

C. Paddock et al., "Transient Thermoreflectance from Metal Films", May 1986 vol. 11, No. 5 Optical Letters, pp 273-275.

C. Paddock et al., "Transient Thermoreflectance from Metal Films", J. Appl. Phys. 60(1), Jul. 1, 1986, pp 285-290.

Per-Eric Nordail et al. "Photothermal Radiometry", Physica Scripts, vol. 20, 659-662, 1979.

A. Rosenwaig, "Thermal Wave Monitoring and Imaging of Electronic Materials and Devices", pp 73-109.

A. Rosenwaig, "Applications of Thermal-Wave Physics to Microelectronics", VLSI Electronics, Microstructure Science vol. 9, 1995, pp 227-288.

W. Lee Smith et al., "Voids, Notches and Microscracks in Al Metallization Detected by Nondestructive Thermal Wave Imaging", Jun. 23m 1989, pp. 211-221.

W. Lee Smith et al., Imaging of Subsurface Defects in ULSI Metalization (AI Voids SI Preciptates, Silicide Instability) and SI Substrates (D Defects), Technical Proceedings Simicon/Japan 1992, Nippon Convention Center, Japan pp 238-246.

W. Lee Smith, "Nondestructive Thermal Wave Imaging of Voids & Microcracks in Aluminum Metallization", 1989 WLR Final Report, pp 55-68.

W. Lee Smith, "Direct Measurement of Stress-Induced Void Growth by Thermal Wave Modulated Optical Reflectance Imaging", 1991 IEEE/IRPS, pp 200-208.

W. Lee Smith, "Evaluating Voids and Microcracks in Al Metalization", Semiconductor International, Jan. 1990, pp 232-237.

C. G. Welles et al., "High-Resolution Thermal Wave Imaging of Surface and Subsurface Defects in IC Metal Lines", Materials Research Society, SF Marriott, Apr. 27-May 1, 1992, pp 1187-1191.

J. A. Batista et al., "Biased MOS-FET and Polycrystalline Silicon Tracks Investigated by Photothermal Reflectance Microscopy", pp 468-469.

L. Chen et al., "Meta-Probe: A New Generation Photothermal System For Thin Metal Films Characterization" (believed to be prior to Mar. 1, 2002).

L. Chen et al., "Thermal Wave Studies of Thin Metal Films and Structures", (believed to be prior to Mar. 1, 2002).

9th International Conference on Photoacoustic and Photothermal Phenomena Conference Digest, Jun. 27-30, 1996 Nanjing, P.R. China, pp 81.

R. S. Sharpe, Research Techniques in Nondestructive Testing vol. VII, Academic Press 1984, pp 158-365.

R. L. Thomas et al., " Thermal Wave Imaging For Nondestructive Evaluation" 1982 Ultrasonic Symposium, pp 586-590.

G. Slade Cargill III, "Electron-Acoustic Microscopy", Physics Today, Oct. 1981, pp 27-32.

A. Rosencwaig, "Thermal Wave Microscopy", Solid State Technology, Mar. 1982, pp 91-97.

Eric A. Ash, "Acoustical Imaging" vol. 12, Plenium Press, Jul. 19-22, 1982, pp 61-65.

U.S. Appl. No. 09/095,805 entitled "Apparatus and Method For Measuring A Property of a Layer in a Multilayered Structure".

U.S. Appl. No. 10/722,724 entitled "Apparatus and Method For Measuring A Property of a Layer in a Multilayered Structure".

U.S. Appl. No. 10/090,316 entitled "Apparatus and Method For Measuring A Property Of A Layer In A Multilayered Structure".

U.S. Appl. No. 09/521,232 entitled "Evaluating A Property Of A Multilayered Structure".

U.S. Appl. No. 10/977,380 entitled "Evaluating A Property Of A Multilayered Structure".

U.S. Appl. No. 09/788,273 entitled "Evaluating Sidewall Coverage In A Semiconductor Wafer".

U.S. Appl. No. 10/090,262 entitled "Evaluating A Multilayered Structure For Voids".

U.S. Appl. No. 10/984,463 entitled "Evaluating A Multilayered Structure For Voids".

U.S. Appl. No. 10/090,287 entitled "Identifying Defects In A Conductive Structure Of A Wafer, Based On Heat Transfer Therethrough".

U.S. Appl. No. 10/979,397 entitled "Evaluation Of Openings In A Dielectric Layer".

J.M. Ziman, F.R.S., "Principles of the Theory of Solids", 2nd Edition, Cambridge At the University Press 1972, pp 278-282.

Chung Wah See and Mehdi Vaez-Iravani, "Differential amplitude scanning optical microscope: theory and applications", Applied Optics vol. 27, No. 13, Jul. 1, 1988, pp 2786-2792.

International Search Report in PCT/US03/06250 which claims priority of U.S. Appl. No. 10/090,287.

Written Opinion in PCT/US99/12999 which claims priority of U.S. Appl. No. 09/095,805.

Communication Relating To Results of Partial International Search in PCT/US05/009588, which claims priority of U.S. Appl. No. 10/813,407 (current application).

International Search in PCT/US05/009588, which claims priority of U.S. Appl. No. 10/813,407 (current application).

Written Opinion in PCT/US05/009588, which claims priority of U.S. Appl. No. 10/813,407 (current application).

* cited by examiner

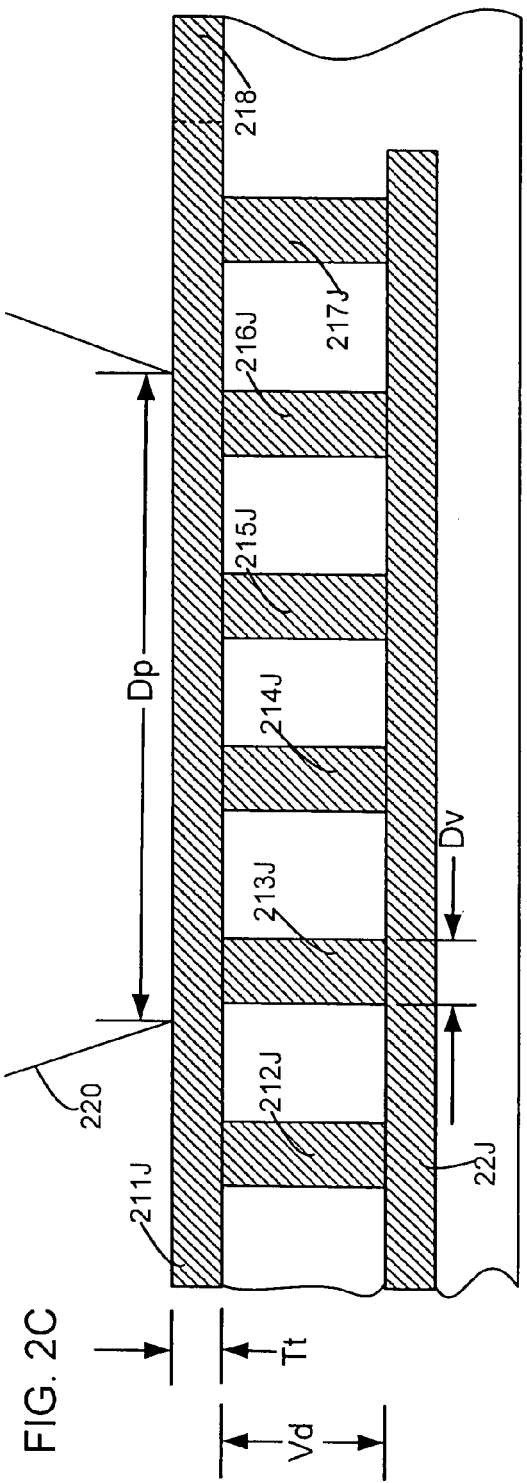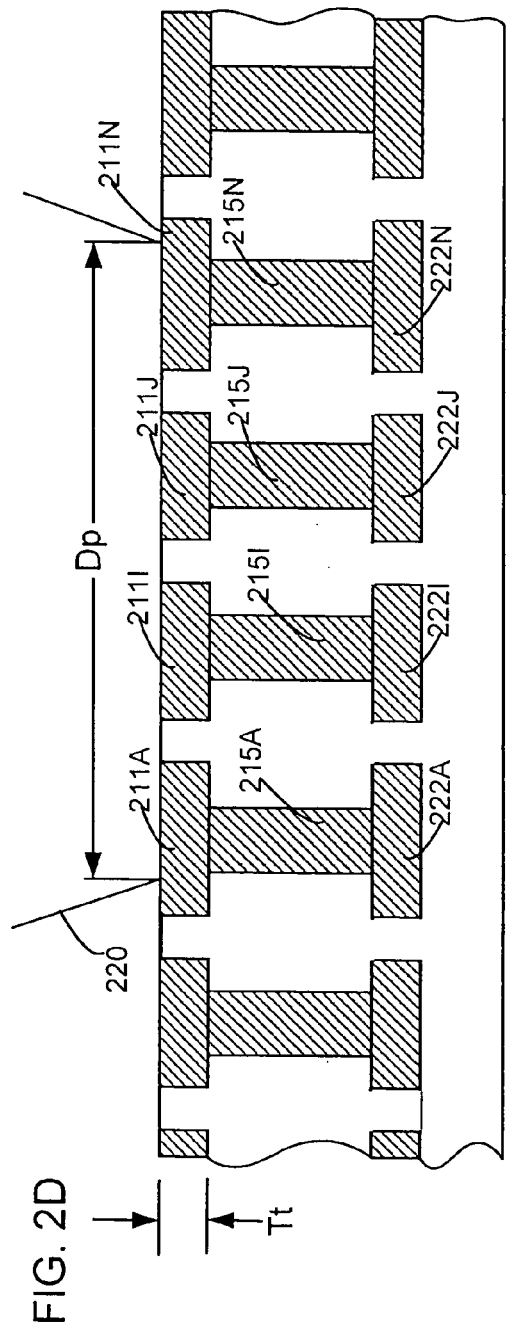

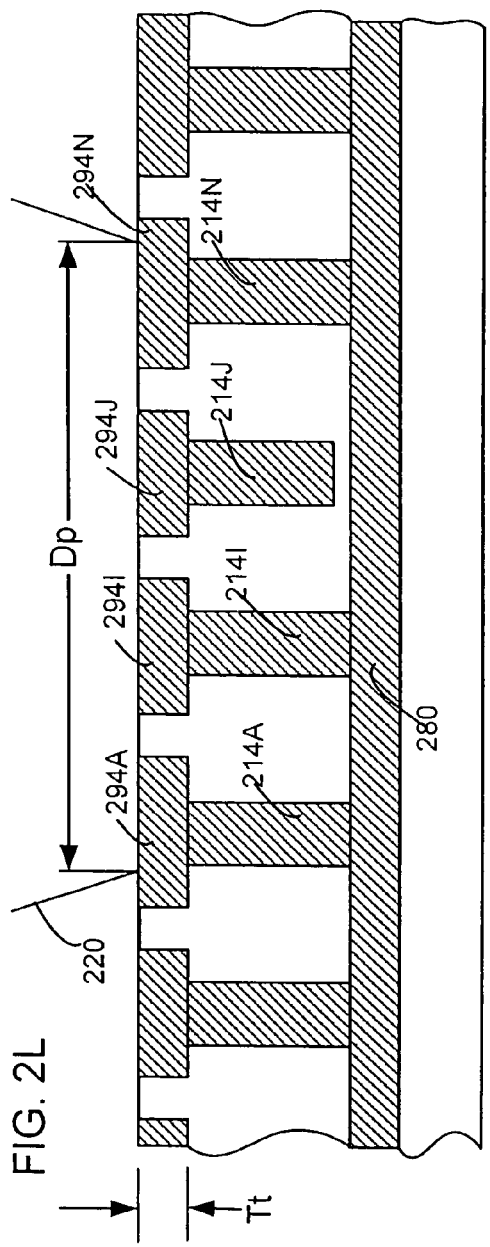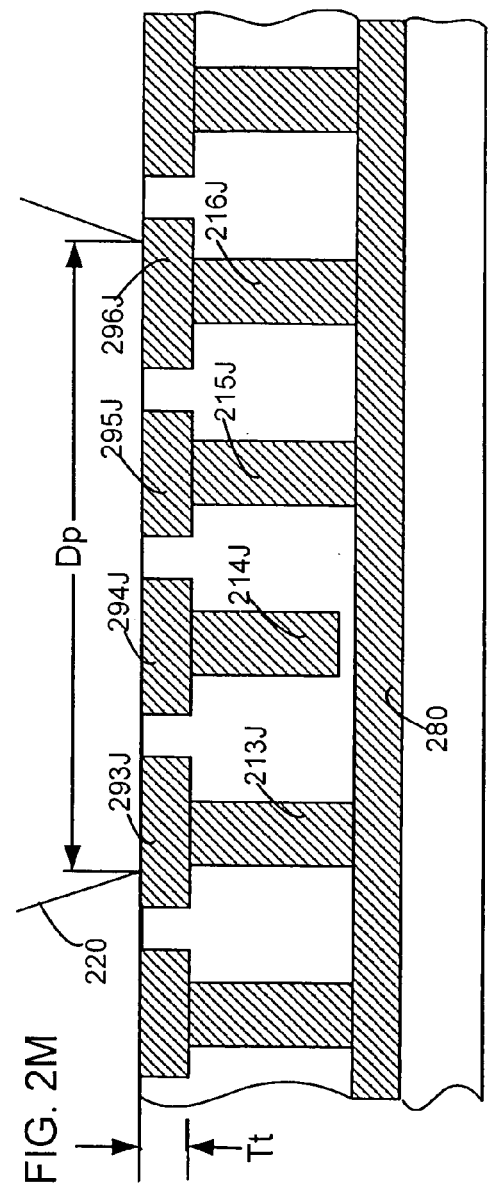

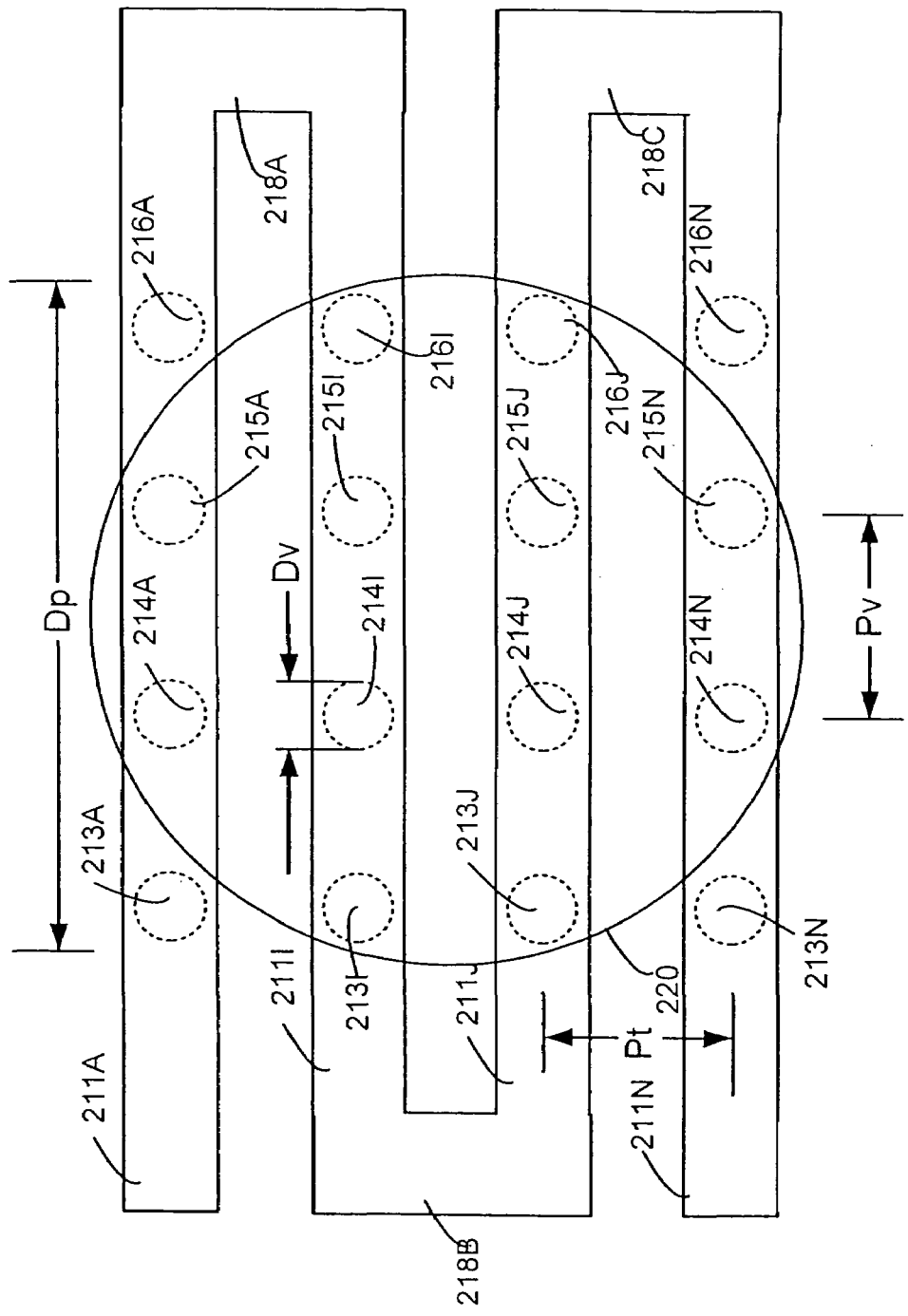

HIGH THROUGHPUT MEASUREMENT OF VIA DEFECTS IN INTERCONNECTS

US APPLICATIONS INCORPORATED BY REFERENCE

This application incorporates by reference herein in its entirety the commonly owned and concurrently filed U.S. patent application Ser. No. 10/812,817, Client Docket 008369USA, entitled "Full-frame thermal pump-probe technique for detecting subsurface defects" filed by Daniel I. Some.

This application also incorporates by reference herein in its entirety the U.S. Provisional Application No. 60/459,908 entitled "Full-frame thermal pump-probe technique for detecting subsurface defects" filed Apr. 1, 2003 by Daniel Some.

This application also incorporates by reference herein in its entirety the U.S. patent application Ser. No. 10/090,287 and entitled "Identifying Defects In A Conductive Structure Of A Wafer, Based On Heat Transfer Therethrough", filed Mar. 1, 2002 by Peter G. Borden et al.

BACKGROUND

Integrated circuits (ICs) use metal lines to connect the various circuit elements together. These lines are called interconnect structures. Because a high density of circuit elements and connections is required, it is necessary to use several levels of metal lines. Each level contains a planar structure of metal lines, with layers of an insulator such as silicon dioxide used to separate the levels from one another.

It is necessary to interconnect the layers to one another, to enable current to flow between the layers. These interconnections are called vias. Vias are located in small holes formed in the insulator, and are commonly 0.1 µm in diameter or larger. These holes are filled with a metal to form an interconnection between metal lines in different layers. Such interconnections must be continuous from a lower level of metal to a higher level. If an interconnection is not continuous, the via will be "open". This defect may cause failure of the integrated circuit.

Open vias can result from a number of process problems. For example, the process of filling the small holes with metal may not fully fill a hole. A residue from a previous process step may impede connection, or the residue may be corrosive and etch away a connection that was properly formed. Such a problem might result in an open via. Also, the formation of subsequent layers of metal requires thermal process steps that may cause a properly formed via connection to "pull back", leaving a partial connection.

Note that the word "defect" or "failure" is here used to mean not only an open via (discussed above) but also a via connection with greater resistance than a perfectly-formed via (i.e. a fully conductive via). For instance, a perfectly-formed via may have a resistance of 1 ohm, and a partially conductive via may have a higher resistance of 2 ohms (i.e. the resistance is two or more times larger for a defective via than for a perfectly-formed via).

In addition, the formation of a patterned layer of metal on top of another layer requires registration of the lithographic pattern. If the pattern is misaligned, vias from one layer may not land or only partially land onto an underlying metal line, resulting in an "unlanded" or "partially landed" via, which forms a fully open electrical connection, or only a partial electrical connection.

A number of methods of testing vias are available. One method of reliably testing interconnections is electrical testing. For example, a via chain is fabricated and probed for continuity. A via chain is a set of short line segments of conductive material alternating between two layers, connected with vias.

FIG. 1A shows such a via chain 100 as a multi-level interconnect structure formed in a wafer with two layers 113 and 114 formed over a substrate 110. The wafer may have transistors and other devices fabricated within it. Various line segments 131a to 131f and 132a to 132n in chain 100 may be made of a metal such as copper, and are embedded within interlayer dielectric layers 111 and 112. Vias 133a to 133l are shown that interconnect the various line segments in layers 113 and 114 to one another. Vias 133a–133l may have a height (separation distance between layer 113 and 114) on the order of 0.2 to 1.0 µm. Metal line segments (also called simply "lines" or "traces") 131a to 131f in layer 114 may be 5 µm long and 0.25 µm wide. Metal line segments 132a to 132n in layer 113 are also of the same dimensions in this example. These line segments are connected to form a chain, by vias 133a to 133l.

Various types of defects can form in vias 133a–133l. For example, small voids can form therein, reducing the cross-section of the via and increasing the resistance. The via hole can be over- or under-etched, causing a change in its size and thereby decreasing or increasing the resistance. A common problem is a failure at the landing site—the point of contact of the via to the underlying line, labeled as site 106 for via 133a contacting to line layer 114. This failure arises, for example, from etch residues left as a result of the formation of the via hole in layer 112. The failure can also arise from thermal stress during the formation of additional metal line and insulator layers above layer 113. The failure is often not an open connection, but a connection of increased resistance. This is a site of potential future failure, since the increased resistance can cause heating when current flows through the via during operation of the integrated circuit.

A significant property of a completed via is its resistance. The frequency distribution of resistance of completed vias is shown in graph 150 of FIG. 1B as line 151. The frequency distribution has a mean value 155. It drops to zero for values of resistance 153 and below, value 153 representing the "over-etched via" described above. In a well-controlled process, an ideal via would have a resistance at value 155. Distribution 151 has a one standard deviation width 152. Values beyond resistance 154 are considered open or failed vias. For an integrated circuit with 5×10^7 vias, this resistance must be greater than the mean value 155 plus six times the standard deviation 152 to ensure a failure rate of less than 10% of the integrated circuits due to bad vias (one in 5'10^8 vias is bad).

A problem in determining the quality of vias is that prior art measurement methods are only able to distinguish completely open vias (vias with no connection whatsoever, some of which may still have too high a resistance to be considered good from the standpoint of circuit function). Consequently, it is necessary to measure a large number of vias to find a small number of bad ones. The conductivity of a chain of vias 133a–133l can be measured by use of probes 140a and 140b (FIG. 1A) that contact chain 100 at the ends of the via chain. To measure the continuity of the chain, an electric current is passed there-through and measured. This method allows a single measurement to determine the continuity of a large number of vias in the chain.

However, such probing has a number of drawbacks when used during manufacturing. First, the just-described "contact" method requires a large area in a production wafer to hold a via chain that is otherwise not a part of a circuit being manufactured. Second, the contact method requires probes to make a contact with chain 100 which may be undesirable during fabrication, since any contact can generate particles and contamination. Third, the contact method cannot be used if a dielectric layer covers the metal lines in layer 113 because the probes need to be in electrical contact with the two ends of the chain 100. Finally, the contact method provides only a single measurement value corresponding to the average via resistance, and cannot isolate individual vias or evaluate a small number of vias in the via chain (unless more complex matrix structures are built that require a large additional area for pads (large metal squares) where the probes contact the structure. Such use of wafer area is undesirable in manufacturing, since the area is not available for product.).

Other methods of examining vias in a wafer relate to various applications of scanning electron microscopes (SEMs). One of these methods is called voltage contrast. Suppose, for example, that vias 133b and 133c are both open. Metal line 132b will then be electrically floating. Under SEM scanning, this segment 132b will charge with electrons and therefore stand out in an SEM image. The limitation of voltage contrast is that it cannot be used with partially failed vias, since any via continuity in a partially failed via will discharge the charge from the segment.

Also, this method cannot be used once a dielectric layer (not shown in FIG. 1) is formed over the segment, since the dielectric will charge up. Therefore, voltage contrast is only usable when the top layer is a metal layer, and cannot evaluate via problems induced by the process of formation of subsequent layers. Moreover, such a prior art measurement is typically used to detect via defects with a resistance above 10 megohms. There is a resistance range from below 10 ohms to over 10 megohms where a via failure is hard to detect. This is also called a "soft failure".

Another SEM method is sectioning. A sample wafer is broken, or a focused ion beam is used to cut away material, exposing a side view of the via. The SEM can then image the via. This method has limitations of being destructive and slow, and is therefore limited to post-analysis of failures.

Another method was disclosed by Smith et al. in U.S. Pat. No. 5,228,776 that is incorporated herein by reference as background. In this patent, a modulated laser beam creates a thermal wave in a metal line. Specifically, Smith et al. state "By this arrangement, the pump beam can be focused on a metal line in one layer while the probe beam is focused on a line in a different layer. Using this approach, it can be relatively easy to find a flaw in a via which is used to connect the two lines." Smith et al. also state that " . . . the assignee's Thermaprobe Imager device is a non-contact technique. However, identification of defective vias has been hampered because the surfaces associated with defective vias are often not optically flat. More particularly, the surfaces can be dimpled, angles, rough or otherwise geometrically distorted and therefore tend to scatter light making reflected power measurements difficult." Smith et al. further state "First, both the pump and probe beams can be focused on optically flat surfaces even if there are intermediate geometrically distorted surfaces associated with a defect."

Smith et al.'s method suffers from two drawbacks. First, thermal waves can reflect from interfaces, such as the end of a line, a bend in a line, or a via connection. Such reflections can perturb measurements based on thermal waves that are described by Smith et al. Second, Smith et al. require that the two laser beams must be independently focused at different sites, which can require complicated optical positioning that varies with circuit geometry.

Vias that are only partially conductive can also be found as described in U.S. patent application Ser. No. 10/090,287 that is incorporated by reference above. As described therein, heat is applied to a conductive structure that includes one or more vias, and the temperature of the conductive structure is measured. Then the measured temperature is checked to identify an irregularity (e.g. by comparison with a predetermined limit, or by finding aperiodicity in a scan of a periodic structure). If an irregularity is found in the structure, the wafer is rejected and if there is no irregularity, the wafer is further processed in the wafer fabrication process.

The just-described patent application describes a method of making a number of measurements along the length of a structure, to obtain a sequence of measurements indicative of properties of structure along the length. The measured signal changes with distance, wherein the signal variation depends on the conductivity of various elements (such as vias and traces) that form the structure. Specifically, if vias are arranged periodically in space with a fixed pitch separating two adjacent vias, then the intensity of a signal measured therefrom is periodic as illustrated by FIG. 5 of U.S. patent application Ser. No. 10/090,287. A Fourier transform of the measured signal shows a sharp peak at the spatial frequency, wherein the spatial frequency is inversely related to the pitch of the vias in the structure.

However, when applying the above-described method in an industrial environment, inventors of the current application note that the method is slow because it requires closely spaced measurements on via chains. This is because periodicity (in case of a structure that has vias located at regular spatial intervals, i.e. a fixed pitch) must be noticeable from the measured signal (as a function of distance along the length of the structure). The step size is typically small, on the order of a fraction of the beam diameter (typically <0.5 μm step size). If larger steps are taken, it is uncertain that the beam's spot will be exactly aligned relative to the periodic structure, with the result that an error in alignment causes large swings in the measured signal due to difference in spatial periodicity between the structure and the measurement locations (rather than due to a change in via resistance).

SUMMARY

In accordance with the invention, a region of a semiconductor wafer that contains a number of vias is heated over time and a temperature of the region as a whole is measured as a function of temporal change in heat being applied. Any significant deviation in the measurement (e.g. from a predetermined reference or from adjacent regions in the same die or another die) is used as an indication of failure of one or more vias in the region being evaluated. A deviation may be deemed to be significant, for example if a predetermined threshold for an attribute of the measured signal is exceeded or alternatively if the measured signal is found to be aperiodic in space although a periodic structure in the region is scanned.

The above-described method is used to evaluate regions wherein vias electrically connect conductive material in an upper layer of the wafer to an underlying layer of conductive material. In some embodiments, the upper layer may be patterned to form traces whereas the lower layer may or may not be patterned depending on the embodiment. Other embodiments apply the above-described method to a test structure wherein the top layer contains islands of conductive material that are isolated from one another in the top layer but each island is electrically and thermally connected to an unpatterned underlying layer by one or more vias. In such a test structure, if a via of an island has a defect, then that island is heated up more than other adjacent islands and therefore the measurement therefrom exceeds the predetermined threshold. In several embodiments, such a region containing multiple islands is heated as a whole, in any manner well known in the art, and the intensity of the applied heat is changed over time, in periodic or aperiodic manner.

Two alternative embodiments measure a change in temperature of the region at the same frequency as a corresponding change in intensity of the applied heat by use of (1) a passive sensing system such as a thermal imager used without a probe beam or (2) an active sensing system that illuminates the region being evaluated with a probe beam and measures reflectance of the probe beam. The measured temperature change is used, in accordance with the invention, as an indication of conductivity of vias that are located in the region being evaluated. Although in some embodiments such a region contains isolated conductive islands in the top layer, the evaluated region of other embodiments may have no islands whatsoever.

In some embodiments, a beam of electromagnetic radiation having a wavelength that is greater than or equal to the pitch between vias is used to apply heat directly to the region being evaluated, thereby to ensure that multiple vias are heated, instead of a single via is being heated. Also, instead of using electromagnetic radiation to apply heat to the region being evaluated, a beam of electrons can also be used to apply heat, depending on the embodiment. In some embodiments, any attribute (e.g., intensity or optical phase) of a portion of an electromagnetic beam that is reflected by the region is measured.

When more than one via is being heated as described herein (e.g. with radiation of wavelength greater than the pitch), the reflected light and an electrical signal generated therefrom does not resolve to an individual via in the illuminated region, and instead indicates an average measure of conductivity of a number of vias that are within the illuminated region. For this reason, the measured signal of several embodiments does not have a spatial periodicity equal to the pitch of vias in the conductive structure. In other embodiments, the measured signal does have one component with spatial periodicity equal to the pitch but this component is ignored (e.g. filtered out). Although the measurement does not resolve to each individual via, if even one of the vias in the illuminated region has greater impedance than the others, the average impedance (and hence reflectance) increase. The predetermined threshold may be selected in some embodiments to give an indication of failure of even a single via.

Many embodiments of the type described above check if the illuminated region (or a portion thereof) has greater reflectance (or higher temperature) than one or more adjacent regions also having the same conductive structure, and whether the measurement has changed significantly therefrom. For example, if the measured signal increases by 100% in the region being evaluated (or just in a single island of the region, depending on the resolution of the measurement), then such a change is deemed to be an indication of failure of one or more vias in the region. In some embodiments, the just-described measurement is repeatedly obtained, in regions adjacent to the just-described region, and also in additional regions that are in turn adjacent to the just-described adjacent regions. These measurements are made in a localized portion of the wafer, e.g. all measurement regions may cover an array of conductive lines or cover islands all of which are located within a single die, or in a street (also called "scribe line") located between two adjacent dice.

Such measurements are then analyzed, to check whether any one measurement deviates from other measurements, e.g. by comparison with an average (statistical mean, or median or mode), in a significant manner. If a significant deviation is found, then the semiconductor wafer is marked as having one or more defective vias, and a process parameter that is used in fabrication of the semiconductor wafer is changed. If there is no significant deviation, then the semiconductor wafer is deemed to be acceptable, and fabrication of that semiconductor wafer is continued, in the normal manner.

Depending on the embodiment, any of a number of different methods may be used to identify the amount of deviation in the measurements that is to be considered significant, e.g. to set the predetermined threshold. Specifically, in some embodiments, any measurement that happens to be greater than the average by more than three times the standard deviation (i.e. $>3\sigma$ or greater than three sigma) is deemed to indicate the existence of a defective via in the area being evaluated. However, in other embodiments, other limits (e.g. $>2\sigma$ or even $>\sigma$ in different embodiments) may be used e.g. if a wafer fabrication process is known to fabricate wafers with no via defects. The significance of a deviation also depends on other factors, such as the number of vias in the region being evaluated. The significance of a deviation is predetermined in some embodiments based on experiments to correlate deviations to defective vias.

Moreover, although a statistical measure is used as a limit in some embodiments, other embodiments may set a non-statistical limit on the signal being measured, based on calibration with wafers that are tested and found to be good. For example, a defective via may cause a signal measurement (of the type described above) to become two (or more) times greater than the corresponding signal measurement obtained when the via is not defective, and in such a case, any measurement that exceeds the average by 50% may be deemed to indicate a defective via. In still other cases, the average resistance of vias may be correlated to the measured signal and an acceptable range for the via resistance may be predetermined. When a signal measurement (of the type described above) indicates that the via resistance is out of this predetermined range for a wafer currently under evaluation, then a defective via or a region containing a set of defective vias is identified.

BRIEF DESCRIPTION OF THE DRAWINGS

FIGS. 2C and 2D illustrate, in cross-sectional views, the structure of FIG. 2A with the coincident laser beams.

FIGS. 2K, 2L and 2M illustrate, in a plan view and two cross-sectional views respectively, the structure of FIG. 2J.

FIG. 2O illustrates, in a plan view, a structure similar to the structures in FIGS. 2A but with conductive material in the upper conductive layer being patterned as a serpentine.

DETAILED DESCRIPTION

Figure 2A:
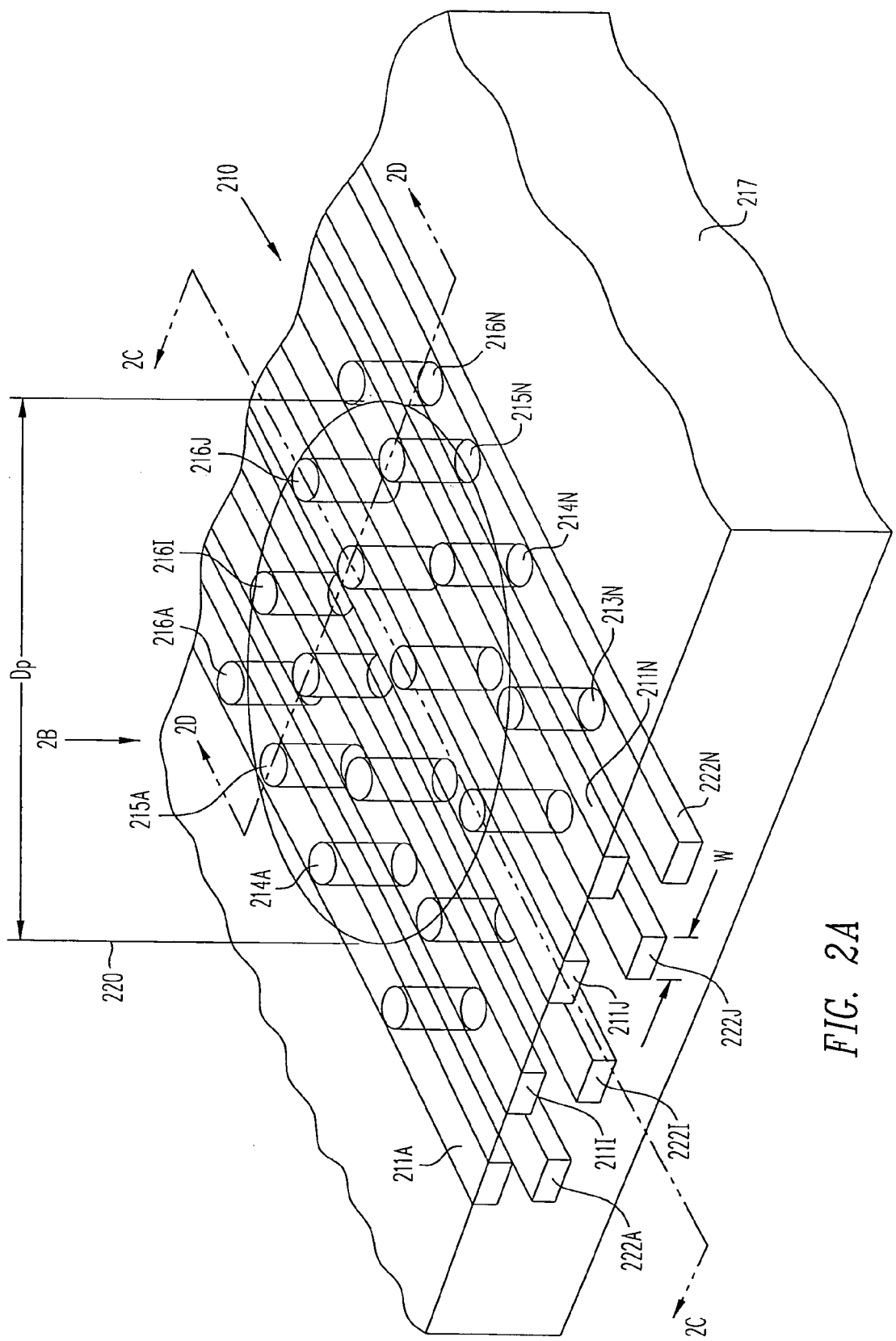
FIG. 2A illustrates, in a three-dimensional view, a multiple level interconnect structure that is evaluated by two coincident laser beams used in accordance with one embodiment of the invention.
Figure 2B:
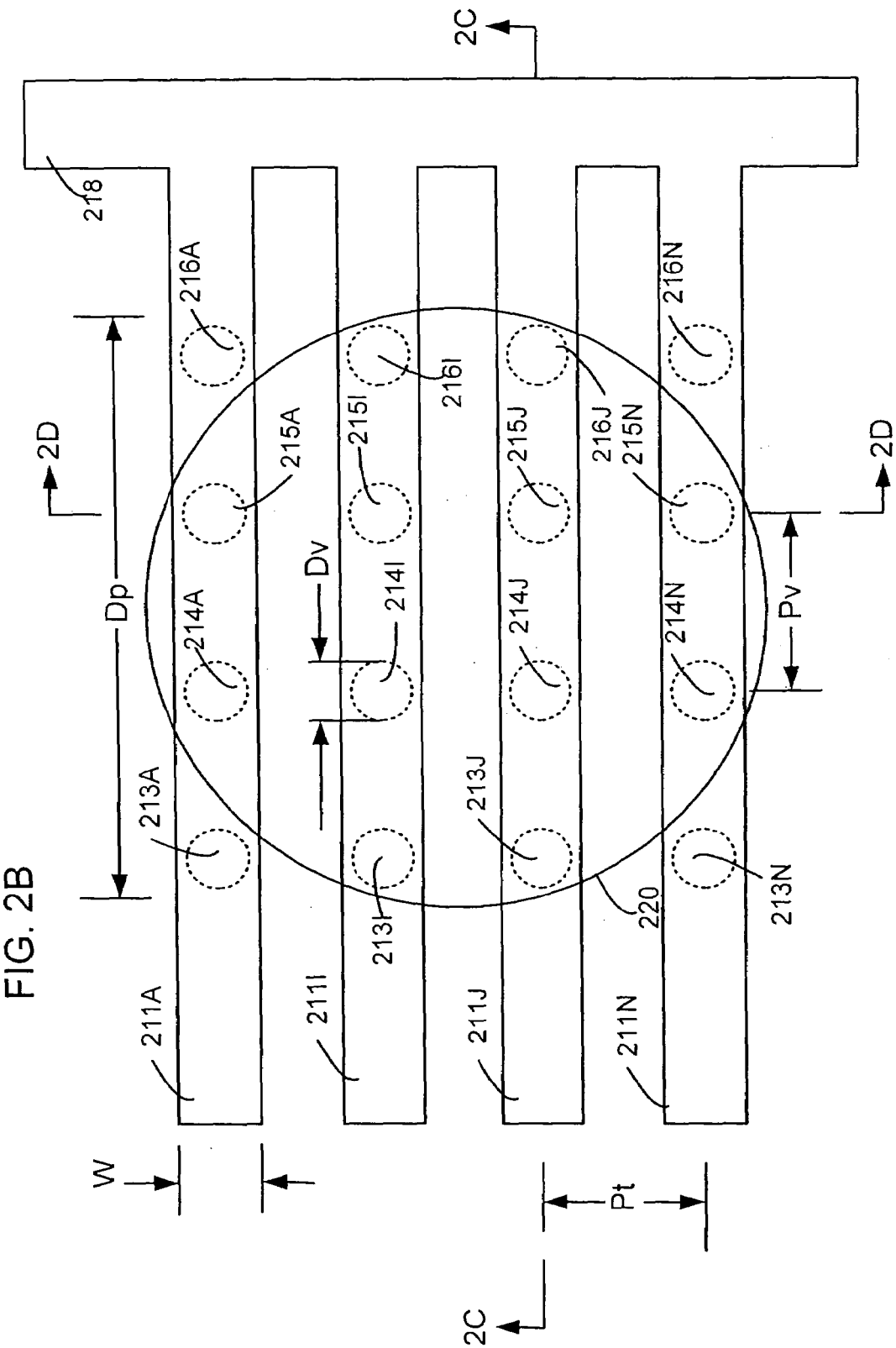
FIG. 2B illustrates, in a plan view, the structure of FIG. 2A in the form of a comb, with the coincident laser beams.

In accordance with the invention, a probe beam 220 (FIG. 2A) is used to illuminate a region of diameter Dp on a semiconductor wafer 217 that contains a structure 210 formed of a number of vias 213A–213N, 214A–214N, 215A–215N and 216A–216N. Note that although vias 213A–213N, 214A–214N, 215A–215N and 216A–216N are illustrated in FIGS. 2A and 2B as reaching a top surface illuminated by probe beam 220, this is merely shown for illustration and it will be apparent to the skilled artisan that these vias end at a lower surface of a conductive layer of wafer 217. Such a conductive layer may form conductive lines (also called traces) 221A–221N in wafer 217 in some embodiments, although other embodiments may pattern the conductive layer differently. Also note that the structure 210 illustrated in FIG. 2A has a number of additional vias which are not shown, i.e. only a few vias 213A–213N, 214A–214N, 215A–215N and 216A–216N are shown although a large number of vias are present in wafer 217.

As shown in FIGS. 2A, 2C and 2D, vias 213A–213N, 214A–214N, 215A–215N and 216A–216N electrically connect conductive lines 211A–211N of an upper layer at the surface of the wafer 217 to a corresponding number of traces 222A–222N in an underlying layer (formed of conductive material). Note also the underlying conductive layer in wafer 217 could be a two-dimensional metal sheet (e.g. see the sheet 280 in FIG. 2J) that is connected to multiple rows of vias that are being evaluated. However, as shown in FIG. 2A, in some embodiments, the lower conductive layer is patterned into lines, each of which only connects to a single row of vias.

Depending on the embodiment, vias 213A–213N, 214A–214N, 215A–215N and 216A–216N may be included either in a real-life structure 210 that is a normal part of circuitry in an integrated circuit die in wafer 217 or alternatively included in a test structure that is fabricated as a non-operational portion of wafer 217 (and such a non-operational portion may be included in every die or in every other die of wafer 217). The just-described conductive lines in each of the upper and lower layers may have a thickness Tt for example of 10 microns and width W for example of 30 microns, although lines of other thicknesses and widths may also be used, depending on the embodiment.

Structure 210 that is evaluated (regardless of whether test or real-life) may have the form of a comb, a serpentine, or a via chain, depending on the embodiment. For example, in FIG. 2B, structure 210 has the form of a comb, as shown by a conductive line 218 (on the right side of the figure) that is connected to all conductive lines 211A–211N of the array. If instead, only trace 211A and 211I were connected on the right side of this figure, and if traces 211I and 211J were connected on the left side of this figure, and if traces 211J and 211N were connected on the right side of this figure then a serpentine is formed. If the diameter Dp of a probe beam is selected to be sufficiently larger than the pitch between vias (as discussed below), then even a via chain appears like a set of continuous lines, i.e. there is no perturbation in the measured signal that is caused by the presence or absence of vias in the via chain.

The specific design (e.g. whether serpentine or comb or via chain) of a structure 210 that is evaluated as described herein is not a significant aspect of some embodiments, as long as multiple vias are covered by the diameter of a probe beam, thereby to provide an average measure of conductivity therein. As noted below, structures that use conductive islands (as shown in FIGS. 2J–2N and 2P) form critical aspects of their respective embodiments, because such a structure limits dissipation of heat from a conductive island being heated (and therefore causes a significant (and measurable) increase the reflectance) in the presence of a defect in an underlying via.

Referring to FIG. 2A, a region of diameter Dp which is illuminated by probe beam 220 (and containing vias 213I–213J, 214A–214N, 215A–215N, 216I–216J) is heated, in any manner well known in the art. For example, some embodiments use a heating beam of time-varying intensity (periodic or aperiodic), that illuminates a region of diameter Dp that is coincident with a region also of diameter Dp illuminated by the probe beam 220 (FIG. 2A). Note, however, that in other embodiments the two diameters (of the probe beam and the heating beam respectively) need not be identical. The heating beam can be a laser beam or an electron beam, depending on the embodiment. Note that the word "illuminate" is used generically to mean the area being directly heated by either an electromagnetic beam or an electron beam (i.e. the area on which either beam is directly incident).

Note that the variation of intensity with time can be periodic, i.e. sinusoidal in some embodiments, whereas other embodiments simply sweep through a predetermined range of frequencies, to form a signal that is commonly called a chirp signal. For example, in one embodiment, a single sweep covers the frequency band from 100–400 KHz, and in doing so the intensity is continuously changed (e.g. increased or decreased). The periodic signal or the chirp signal is used primarily for synchronization, so that a reflection of the incident signal can be detected by use of a lock-in detector (such as a lock-in amplifier). The lock-in detector used in some embodiments to measure only the reflection of a probe beam, and to screen out other effects, such as light from a heating beam (for example). Note that any other signal that can be detected by a synchronous detector may be used in other embodiments.

In another embodiment, a measurement of the type described herein is made at a fixed distance from the point of application of heat. In such an embodiment, contact probes may be used to apply heat to one or more conductive lines and a probe beam may be used to measure the temperature. Note however that use of such contact probes while effective in obtaining a measurement as described herein have the drawback of introducing defects during manufacture of integrated circuit dies on the wafer, simply due to making contact. Other means of heating (such as an electron beam and/or an ion beam) may alternatively be used, in other embodiments.

In some embodiments, each of the probe beam and the heating beam are of electromagnetic radiation, and both beams have a wavelength greater than or equal to the pitch (the distance between two adjacent vias). Depending on the embodiment, the two areas being illuminated by the heating and probe beams may be of different diameters and may or may not be concentric (wherein the probe beam illuminated area is smaller than the heating beam illuminated area), instead of being of the same diameter and coincident as illustrated in FIGS. 2A–2D. In some embodiments wherein the areas illuminated by the two beams are not concentric, the illuminated areas are maintained at a fixed orientation relative to one another throughout a given set of measurements, so that the relative orientation does not affect the measurement. Note that in some embodiments that maintain a relative offset between the two beams, the offset is constant so as not to affect calibration.

Next, in several embodiments the intensity of a portion of the probe beam 220 that is reflected by the illuminated region is measured, e.g. by use of a lock-in amplifier tuned to the frequency at which the intensity of the applied heat is changed (e.g. the frequency at which the heating beam's intensity is varied; note that this frequency may be swept within a measurement, such sweeping minimizes sensitivity to fixed frequency noise). As noted above, such a measurement (from the lock-in amplifier) indicates an average measure of conductivity of all vias 213I–213J, 214A–214N, 215A–215N, 216I–216J that are located in the illuminated region (of diameter Dp) of wafer 217. Specifically, heat injected into conductive lines 211A–211N flows along these lines, setting up a temperature distribution with a peak at the center of the heating beam. The peak temperature, which is determined by using probe beam 220 provides a measure of the thermally induced change in reflectance in the metal traces, and corresponds to the line resistance thereof.

When the metal traces are heated, each of vias 213J–216J (FIG. 2C) shunts heat from a conductive line 211J to which it is connected, thereby reducing the temperature under the probe beam 220. The temperature drop caused by any given via 214J (FIG. 2C) is proportional to the quality of the via's connection to the lower layer (e.g. to conductive line 222J in FIG. 2C). An open via (not shown) shunts no heat from line 211J to line 222J, whereas a good via shunts the greatest amount of heat there-between. A partially conductive via between lines 211J and 222J shunts an amount of heat somewhere in between the just-described two extremes.

Figure 2E:
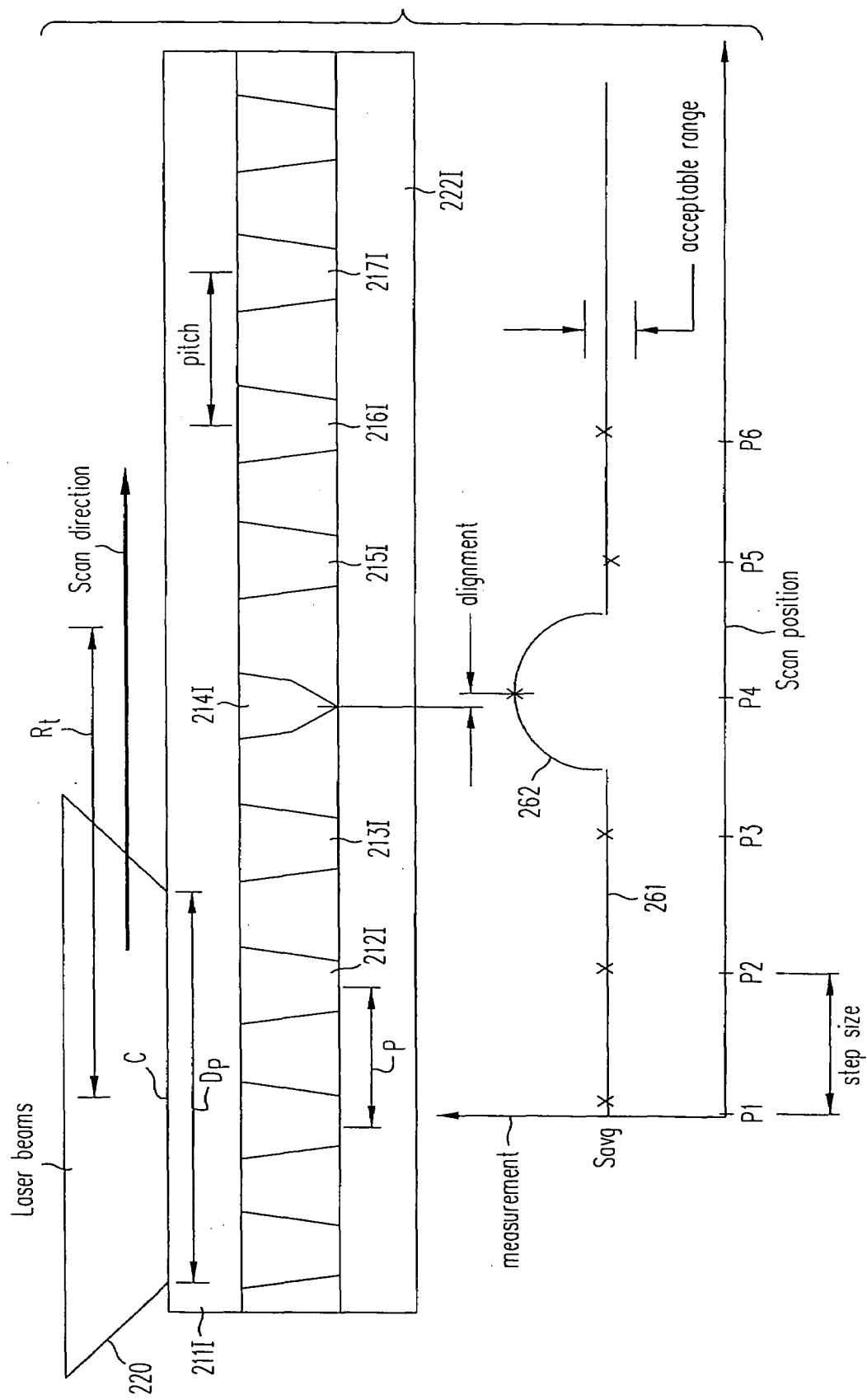
FIG. 2E illustrates, in a cross-sectional view with a graph of the measured signal superposed thereon, the location of a defective via 16J and the corresponding position at which there is an increase in the measurement (each measurement is shown as "x") in accordance with the embodiment illustrated in FIGS. 2A–2D.

The difference in conductivity between vias of various qualities in the structure being evaluated affects the above-described single measurement across all the illuminated vias (as illustrated in FIG. 2E). Specifically, a measurement of the type described herein includes the response of a number of vias 213I–213J, 214A–214N, 215A–215N, 216I–216J that are all contained in the illuminated region. For example, in FIG. 2E, a via 214I is shown to be only partially conductive, and such a via 214I may have a resistance in the range of 10 ohms to 10 megohms, while all other vias 213I–213J, 214A, 214J–214N, 215A–215N, and 216I–216J contained in the illuminated region may be good and have a resistance of 1 ohm. Assume that via 214I does have a resistance of 10 ohms and all the remaining vias have a resistance of 1 ohm, then the average resistance of all vias contained in a region that is illuminated by the beam of diameter Dp (see FIGS. 2B–2D) is 1.75 ohm, which is almost twice the average resistance of 1 ohm if all vias were good.

Therefore, a measurement Sdefect that is obtained when beam 220 covers via 214I (in addition to its surrounding vias) falls outside of an acceptable variance (e.g. ±100 microvolts which is caused by a corresponding variance of ±0.1 ohm) in the average signal Savg (which may be, for example, 1000 microvolts). Note that the measurement Sdefect does not resolve the defective via 214I from among its surrounding vias (therefore it is not known which of the illuminated vias is in fact defective). Instead, Sdefect merely indicates that one of the several illuminated vias is defective. Such an indication is sufficient in some embodiments that merely use such indication to trigger a change in process parameters (either automatically or via manual intervention) for improving the fabrication of future wafers.

The precise value of a variance in the average signal Savg that is sufficient to cause a measurement to be deemed to indicate a defective via in any given embodiment may be determined in any manner, e.g. by experiment over one or more test wafers or by calibration over a test structure in a production wafer, or by correlation to electrical measurement of a chain of vias to determine a relationship between average via resistance and signal.

In one embodiment illustrated in FIG. 2E, measurements over a number of regions at positions P1–P3 along the length of an array of conductive lines are found to fall within an acceptable range around an average Savg. For example, the measurements at P1–P3 may fall within the range 3000±100 microvolts. Thereafter, the next measurement at position P4 may be found to fall outside the range, e.g. this measurement may be 5000 microvolts. In such a case, an approximate location of a partially conductive via (in this case via 214I) has been found. As noted above, at this stage it may be still unknown as to which of three vias that are illuminated during the measurement at P4 is defective, but just the presence of such a via defect is sufficient to trigger a change in process parameters in some embodiments.

Note that analysis of surrounding measurements (e.g. P3 and P5) may indicate the location of the defective via relative to the location of the defective measurement P4. For example, in the example illustrated in FIG. 2P, defective via 214I most strongly affects the single measurement P4 which is obtained when probe beam 220 is centered over conductive islands 298A and 298J. Another measurement P5 which is made next (to the right of measurement P4), when beam 220 is centered over conductive islands 298B and 298K is likely to be same as the average Savg if there are no defective vias being illuminated.

Moreover, a previously made measurement P3 (to the left of measurement P4) may only insignificantly exceed the Savg for two reasons. First, only a small portion of island 298A is illuminated when beam 220 is centered over islands 298C and 298I (during the P3 measurement). Second, since island 298A has three conductive vias that are not defective, 75% of the energy incident thereon (during measurement P3) is dissipated by the three non-defective vias to the underlying layer.

From such analysis it may be determined that it is one of the central eight vias that are illuminated during the single measurement P4 that is defective (because vias 213I and 213J of the partially illuminated islands 298C and 298I on the left side and vias (unlabeled) on the right side for the partially illuminated islands 298B and 298K are eliminated due to the two reasons discussed in the previous paragraph). If it is necessary to specifically and precisely identify which of the eight vias (of the two islands 298A and 298J over which beam 220 is centered) is defective, one may repeat the just-described process in the region between the P3 and P5 measurements, while using a smaller diameter probe beam 220 that provides increased resolution (down to via diameter).

The specific size of a conductive island relative to the number of vias that it covers may be selected by trial and error, based on the specific process being monitored. Typically the fewer the number of vias under a conductive island, the better the likelihood of detection of a defective via. For this reason some embodiments use conductive islands that each have just a few vias underneath (e.g. no more than 12 vias, typically only 4 vias, or in some cases only 1 via). However, other embodiments use conductive islands that each have a substantially larger number of vias, e.g. 100 vias, 300 vias or even 500 vias.

Referring to FIG. 2E, it is to be noted that the precise location of partially conductive via 214I may be different from the precise position P4 at which a deviation in measurement is initially found, e.g. due to misalignment. Even in the presence of an error in alignment, the presence of a partially conductive via is detected by a method of the type described herein, because the measurement at the misaligned position P4 exceeds a preset limit on the measured signal. Even if there is a slightly larger difference in alignment between the spatial location of position P4 (where the measurement is made) and the spatial location of partially conductive via 214I, the same measurement is likely to exceed the preset limit, thereby to indicate the presence of a defective via. If a partially conductive via 214I is located in between two measurements, then the acceptable limit (for the measured value) is selected to ensure that both such measurements exceed the acceptable limit.

Note that several embodiments of the type described herein provide an unexpected benefit over the prior art of electrical testing of vias in a conductive structure. In the prior art, a large chain of vias is measured, providing an average resistance. For example, if a chain has 100,000 vias of average resistance 1 ohm, and a single via has an unacceptable resistance of 100 ohms, then the prior art needs to measure 100, 100 ohms, a barely perceptible change over the 100,000 ohms. In contrast, some methods in accordance with the invention spatially localize defective via measurements (of vias that are smaller in number by several orders of magnitude, e.g. by evaluating 100s of vias at a time), so that a 100 ohm via would easily be identified because the measured signal is doubled (i.e. 200 ohms). Since a small number of defective vias can cause a circuit to fail, the new method of the type described herein is advantageous over the prior art, which cannot resolve potentially fatal defects. A method of the type described herein is also faster than evaluating one via at a time, e.g. if 100s of vias are evaluated in a region, then the testing time is reduced by two orders of magnitude.

In the example illustrated in FIG. 2E, various positions at which each measurement is made (namely P1–P6) are separated from one another by a distance (called "step size") that may be selected to be about the same as the distance between two vias (called "pitch"). In several embodiments, the step size is selected based on the size of the illuminated area, and in many embodiments the step size is typically less than the illuminated area size, so as to provide a continuous measurement over the area, while minimizing spatial variation caused by scanning. In several embodiments, the step size (FIG. 2E) is such that measurements that are affected by a defective via overlap one another. In one exemplary embodiment, heat flows along conductive line 211I for up to a distance Rt (also called "thermal decay length") of about ±3 µm from the center "C" of beam(s) 220 while dissipating to less than 10%. Therefore, measurements may be spaced apart from one another by 3 µm (or even more, e.g. up to 6 µm) along the direction of the via chain's conductive lines.

However, in the transverse direction, the thermal decay length is on the order of the size of the illuminated area, because of the low thermal conductivity dielectric between the conductive lines. For this reason, the measurement spacing is selected in many embodiments to be no greater than the illuminated area size in the direction transverse to the lines. Note that in some embodiments, the step size may be larger than diameter Dp (e.g. 2 µm) of beam(s) 220, because as noted above, a region of radius Rt that is concentric with but larger than the illuminated region is heated by beam(s) 220. In the above-described exemplary embodiment, for measurements with a step size of 3 µm overlap, alignment of beams 220 relative to the location of vias is not an issue. Other embodiments may simply sample an array of vias for variation in signal, and not try to find all defective vias in an area.

In view of the above explanation, it will be apparent to the skilled artisan that a partially conductive via can be detected by measurements made with the step size greater than pitch P (e.g. adjacent vias may be separated by a pitch P of 0.8 µm which is significantly smaller than the step size of 3 µm). As noted above, in some embodiments the thermal distribution drops off beyond a distance Rt greater than half the beam diameter Dp. A partially conductive via should be no more than one thermal decay length Rt away from the center C of the illuminated area, in order for it to be detected in some embodiments.

Therefore, depending on the embodiment, the pitch P between adjacent vias is selected to be less than distance Rt (e.g. typically 3–5 µm). Note there is a tradeoff as follows. When the diameter of beam is kept fixed, a larger pitch P places fewer vias in the illuminated area, so the measurement is more sensitive to variation in a single via (among vias in the illuminated area). A smaller pitch P places more vias in the illuminated area, so the number of vias inspected is greater. This is a trade-off that may be made differently, depending on the embodiment In FIG. 2E, measurements at positions P1–P3 provide a baseline 261 that is more or less constant (i.e. falls within the acceptable range) before a defective via is encountered at position P4 as illustrated by peak 262 and subsequent measurements at positions P5-P6 continue the substantially steady baseline. Note that the term "baseline" is used herein to denote a line (in a graph) formed by connecting a majority of measurements that are substantially identical to one another (e.g. differ from each other no more than 10% or 20% depending on the embodiment). For example, when a current measurement is made, the current measurement may be compared to the previous measurement and if they differ by less than 10% then the current measurement is connected to the previous measurement and if not the current measurement is left unconnected (in which case the previous measurement is compared with the next measurement in order to extend the baseline while the current measurement is left unconnected). Instead of a 10% or 20% limit on the difference between successive measurements, a different number (e.g. based on a statistical measure such as three times standard deviation) may be used in some embodiments when deciding whether to include or exclude a measurement from the baseline.

Figure 2F:
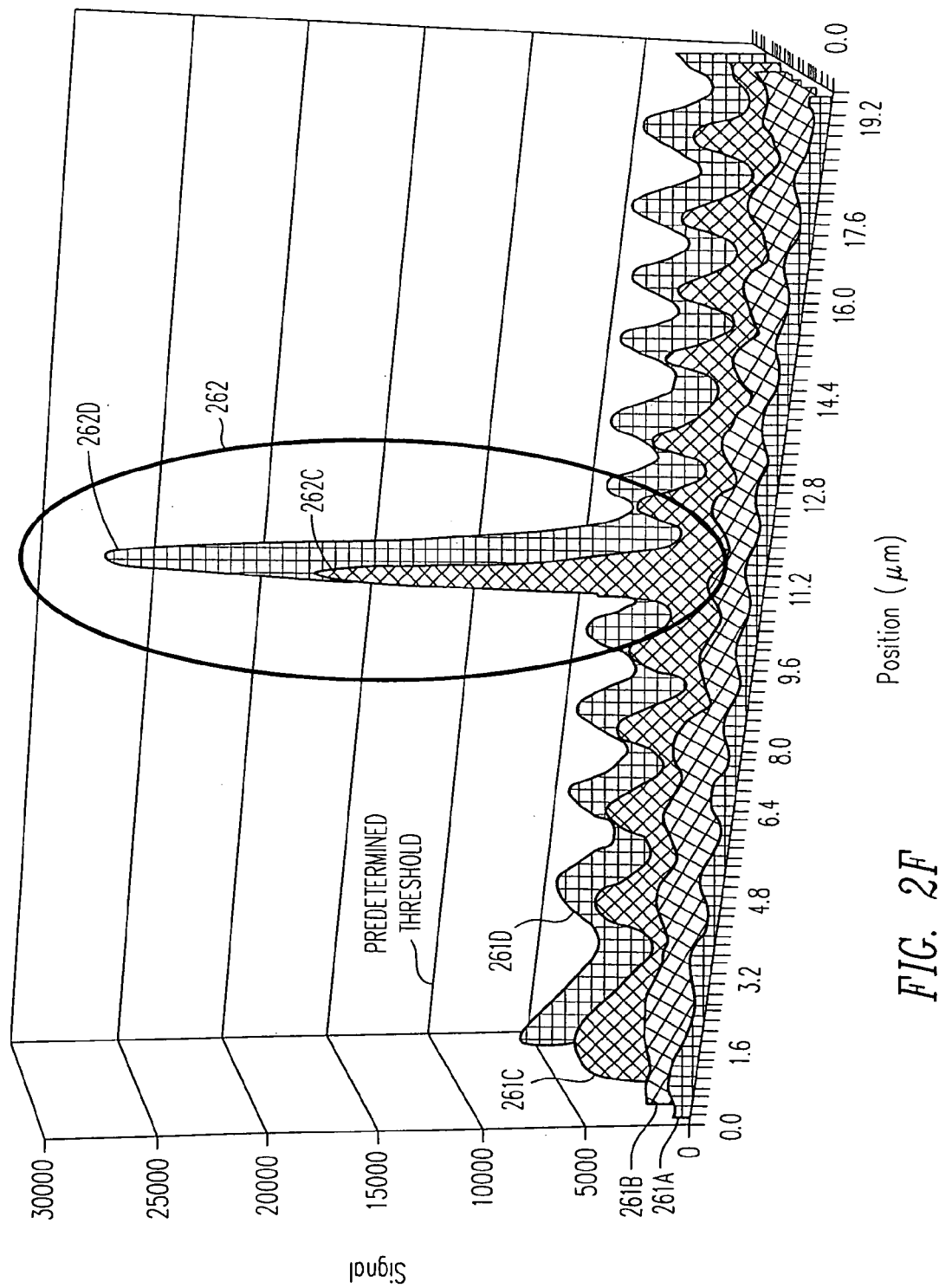
FIG. 2F illustrates, in a three-dimensional graph, a plot of measurements of the type described in reference to FIGS. 2A–2E as a function of via diameter, for good vias (also called "void-free" vias) that form an undulating baseline or a constant baseline, and for partially-conductive vias (also called "voided" vias) that form peaks. Note that in FIG. 2F the Y axis shows a ratio of the voltage from a lock-in amplifier (or AC) signal in μV divided by the DC signal in volts (the latter indicating the reflectance of the structure).

An approximately constant baseline 261 (FIG. 2E) is ensured in some embodiments by making probe beam 220 form an illuminated area of diameter Dp that is sufficiently large to average out a periodic undulation (or other such effect) in space caused by periodicity (or other pattern) in the spatial location of vias or conductive lines in the structure being evaluated. The presence of an undulating baseline in some embodiments is illustrated in FIG. 2F. Specifically, as shown in FIG. 2F, a baseline 261A may be almost constant if the size of the illuminated area is larger than the spacing between lines in the via chain. However, when the conductive lines in the via chain are farther apart than the size of the illuminated area, a corresponding baseline 261B has a larger amplitude of undulation than baseline 261A.

Note that an undulating baseline is not necessarily a limitation of a measurement in accordance with the invention; for example, a baseline's periodicity in space is analyzed and a deviation in spatial periodicity (relative to the periodicity of the conductive structure) is used to indicate the presence of a defect in some embodiments. Furthermore, in the example illustrated in FIG. 2F, two improperly formed vias are identified by the respective peaks 262C and 262D that exceed the predetermined threshold (e.g. the value may be several times the average). Multiple such peaks may together form a single peak 262 in FIG. 2F if probe beam diameter is made so large and the step size is made so large as to cover the two defective vias in only a single measurement).

Note that, if the number of vias that are included in each measurement becomes too large, the effect of certain partially conductive vias (which have a resistance predetermined to be unacceptable) becomes small enough to be lost in noise, even though other partially conductive vias (and open vias) may still be detected. For example, if the diameter Dp is increased to be sufficiently large, vias having a resistance of 15 ohms may remain undetected (assuming the acceptable range has remained unchanged) even though vias having a resistance of 100 ohms are detected (using the same acceptable range). Therefore, the ability to detect partially conductive vias by use of methods of some embodiments is reduced gradually with a corresponding increase in diameter Dp.

For this reason, an appropriate beam diameter Dp is user selected in some embodiments, to be sufficiently large to cover multiple vias, and yet detect vias having the smallest unacceptable resistance. As noted above, a larger size of the illuminated area (i.e. larger beam diameter Dp) gives greater throughput (more vias measured) at a cost of reduced sensitivity to variation in via resistance. The number of vias that are included in a measurement by an embodiment may fall within a range Vmin–Vmax, wherein Vmin is selected to be sufficiently large to average out the periodic undulation (e.g. Vmin=4) and Vmax is selected to be sufficiently small to ensure the individual contribution of any single via remains significant (e.g. Vmax=20). The precise values of Vmin and Vmax depend on a number of factors, such as the signal to noise ratio of the measurement, the spatial periodicity of the location of the vias, the line cross-section (which determines the size of the heated region) and the maximum limit on the resistance of a via that is to be treated as good.

The above-described two acts of (1) illuminating multiple vias with a heating beam and a probe beam, and (2) making a measurement including multiple vias, are performed repeatedly, in a number of regions near the just-described region, e.g. along the length of the array of traces, from left to right thereby to make a scan. Specifically, a scan is performed in some embodiments as illustrated in FIG. 2E, and during the scan a moving average may be maintained of the measurement being made (e.g. over a predetermined number of recent measurements, e.g. 5 measurements, in a linear scan). In some embodiments, if a current measurement exceeds the moving average (e.g. of the last three measurements) significantly then the current measurement is deemed to indicate the existence of a partially conductive via.

Note that scanning across several regions may be implemented in any manner well known in the art. Some embodiments scan the beam(s) along one axis using a galvanometer and move the stage along the other axis. For example, as shown in FIG. 4B, stage 459 may be scanned along the X axis while the optics may be scanned along the Y axis. The details of the scanning mechanisms used are not critical aspects of the invention. Note that scanning along both axes could be implemented with stage motion or alternatively by a 2-axis galvanometer.

In several embodiments of the type described above, the measurement sites are evenly spaced by a distance smaller than the beam diameter. For example, steps of 1 µm may be made with probe beam of diameter 2 µm. In one specific implementation of such a scan, the stepping size is less than the beam diameter, in order to provide a plot of a continuous signal from the scan. In another embodiment, the step size is 2 µm and the diameter of the illuminated area is 2 µm, in which case the step size is greater than the beam radius of 1 µm. In another embodiment, the step size is 2.5 µm, which is greater than the beam diameter but smaller than the thermal decay length of 3 µm. Also, in one embodiment, the location of each via is at a measurement site, although one or more non-via locations may also be used as measurement sites in other embodiments.

In some embodiments, a stage (on which the semiconductor wafer to be evaluated is normally placed) is set in free motion, moving at a speed of 200 micrometers per second, and the measurement signal is read continuously at intervals of 10 msec and stored. Such embodiments provide a signal equivalent to a series of measurements made by stepping and measuring as described above. Such embodiments may obtain a greater noise in the measurement, because of the motion of the stage, and because of the shorter duration of the lock-in integration time, but these embodiments improve the throughput of the measurement method substantially. Therefore, scanning as described herein covers both, the free motion embodiments (in which an analog signal is sampled continuously) as well as the above-described stepping embodiments (also called "hopping embodiments") in which a series of individual measurements are made.

Note that a free motion scan of the probe beam (and heating beam if used) along a conductive line results in a relatively smooth signal response of the type illustrated by the baseline in FIG. 2E. Note the unexpected result obtained when the conductive line has a set of underlying vias and even a single via is partially conductive, in which case an increase in signal is detected (beyond the baseline). Because a periodic background signal of the type described in U.S. patent application Ser. No. 10/090,287 is absent in measurements of some embodiments, the signal to background ratio is high. Therefore, the structure may be scanned at high speed when performing a method of the type described herein.

Several embodiments are based on use of a periodic background signal of the type described in U.S. patent application Ser. No. 10/090,287, and this signal is analyzed for periodicity to provide information about the vias and smaller defects. In such embodiments, deviation from a perfectly periodic signal is used to identify the presence of local via defects.

In some embodiments, when the diameter Dp is sufficiently large to include several tens of vias, the signal-to-noise ratio is very high (about 1000). Reducing the SNR ten-fold to 100 provides a 100× reduction in the measurement time, e.g. to 0.02 seconds/site. When using a site spacing of about 2 μm, the number of sites required to cover an array can be made 2,500 (50×50), in which case the time required to scan the full array is 50 seconds. This is a practical throughput for in-line measurement of via connectivity, i.e. measurement during wafer fabrication.

Figure 2G:
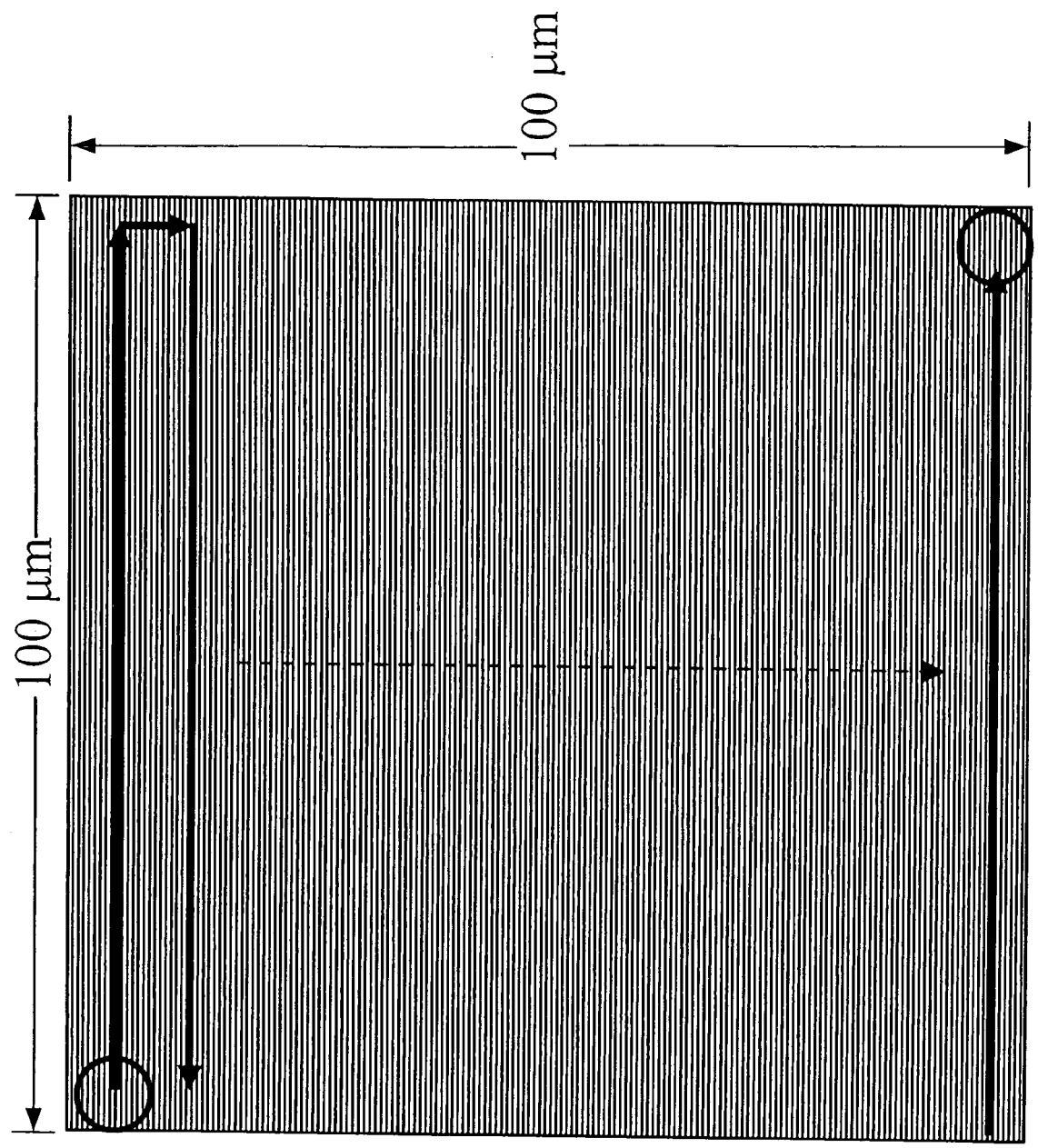
FIG. 2G illustrates, in a plan view, an array of conductive lines that is evaluated in the manner illustrated in FIGS. 2A–2D.

Although a linear scan is illustrated in FIG. 2E, along the direction of the array of conductive lines, an area scan may also be performed as would be apparent to the skilled artisan in view of the disclosure. For example, FIG. 2G illustrates performing a linear scan from left to right followed by moving downward followed by another linear scan from right to left. In this manner a number of linear scans are performed (and a number of measurements are made during each linear scan) until a predetermined area is covered.

Note that during each scan, at each of several locations encountered during the scan, the following acts are performed: the probe beam illustrates a region having multiple vias (as per act 301 in FIG. 3A), an electrical signal is generated indicative of an attribute of a portion of the probe beam reflected by the illuminated region (as per act 302). Note that although scans that are "linear" are used in some embodiments, other embodiments may use non-linear scans, such as a scan from one point to another, but not necessarily following a straight line path (for example, an oscillating path or zig-zag about a conductive line, instead of moving straight along the line), or a scan at a non-constant velocity may be used, depending on the embodiment.

The area covered by a number of such scans may be rectangular or square, depending on the embodiment. Note also that such an area could even have an irregular shape. One embodiment illustrated in FIG. 2G shows evaluation of a 100 μm×100 μm array of fine conductive lines containing on the order of 50,000 μm of copper lines (pitch of 0.8 μm, 50% fill), and on the order of 100,000 vias spaced at 0.4 μm intervals. The just-described array of FIG. 2G is evaluated in one embodiment by a 2 μm laser beam diameter Dp and a 2 second/site measurement time, with 50 measurements along each linear scan, resulting in 50×50 measurements for the entire array. In the just-described example, the conductive lines are each connected to an underlying sheet of conductive material by vias spaced 0.4 μm apart, and having a diameter of 0.14 μm. Note that there are approximately 62,500 vias in a 100×100 μm area of the test structure shown in FIG. 2G.

Figure 2H:
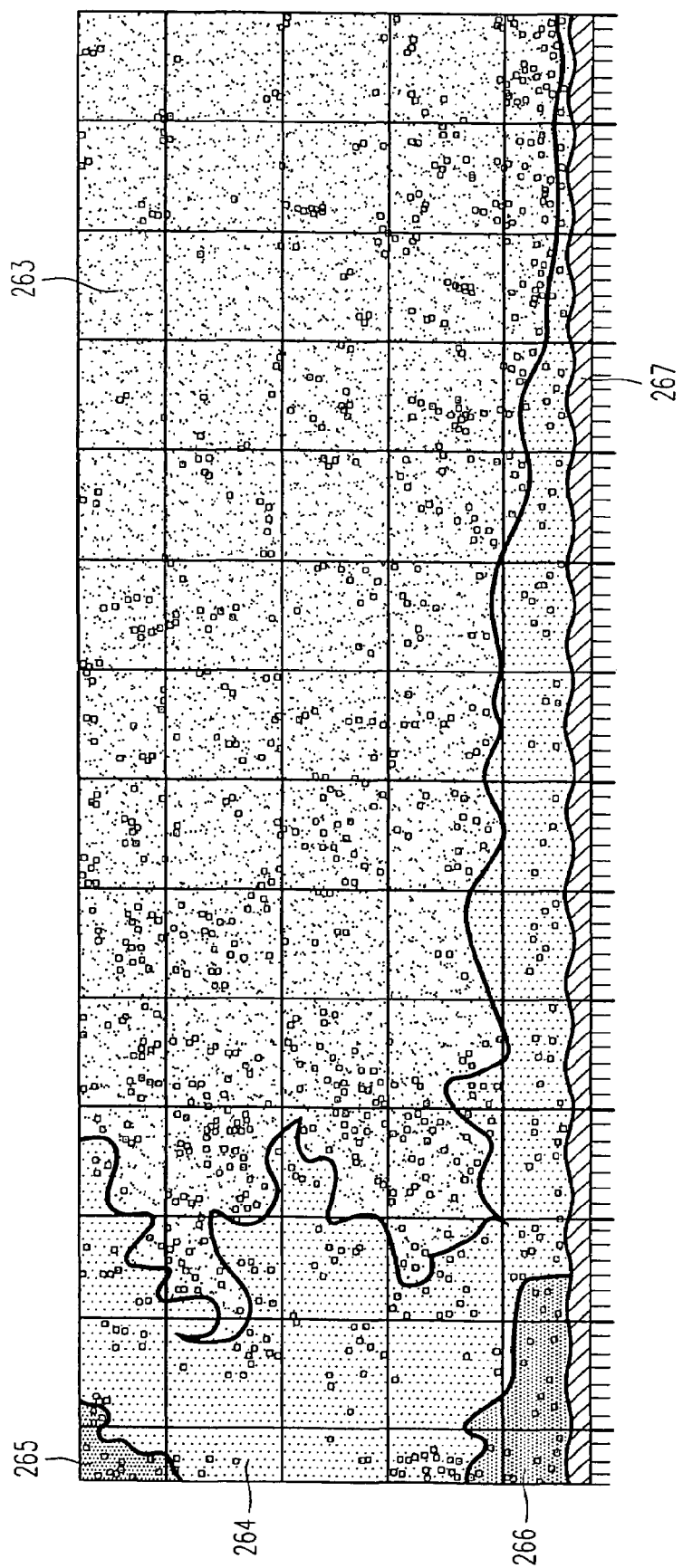
FIG. 2H illustrates, in a plan view, a two-dimensional contour plot from an area scan of the type illustrated in FIG. 2F.

The result of plotting such measurements in a contour map (with signal values of 30000 μV/V and 40000 μV/V setting the limits for each of two contours) is illustrated in FIG. 2H. Note that in FIG. 2H, the dots represent regions of slightly higher via resistance (relative to the adjacent regions). Moreover, the area 264 on the left side of FIG. 2H has been under-etched, and the via diameters are smaller, which results in an overall higher via resistance in this area 264 (and this area also has dots indicating regions of higher via resistance).

As seen from region 263 on the right side of FIG. 2H, most of the measurements fall below 30000 and therefore represent well formed vias. Also, as shown by region 264 on the left side of FIG. 2H, a smaller number of measurements fall within the range 30000 and 40000 and represent partially-conductive vias. Note that in region 267 of FIG. 2H, there are no vias. Efficacy of this embodiment in detecting defective vias is shown by regions 265 and 266, in the top left corner and the bottom left corner of FIG. 2H, wherein the measurement exceeds 60000 indicating that vias in these regions have significantly high resistance, indicative of defects therein.

Figure 2I:
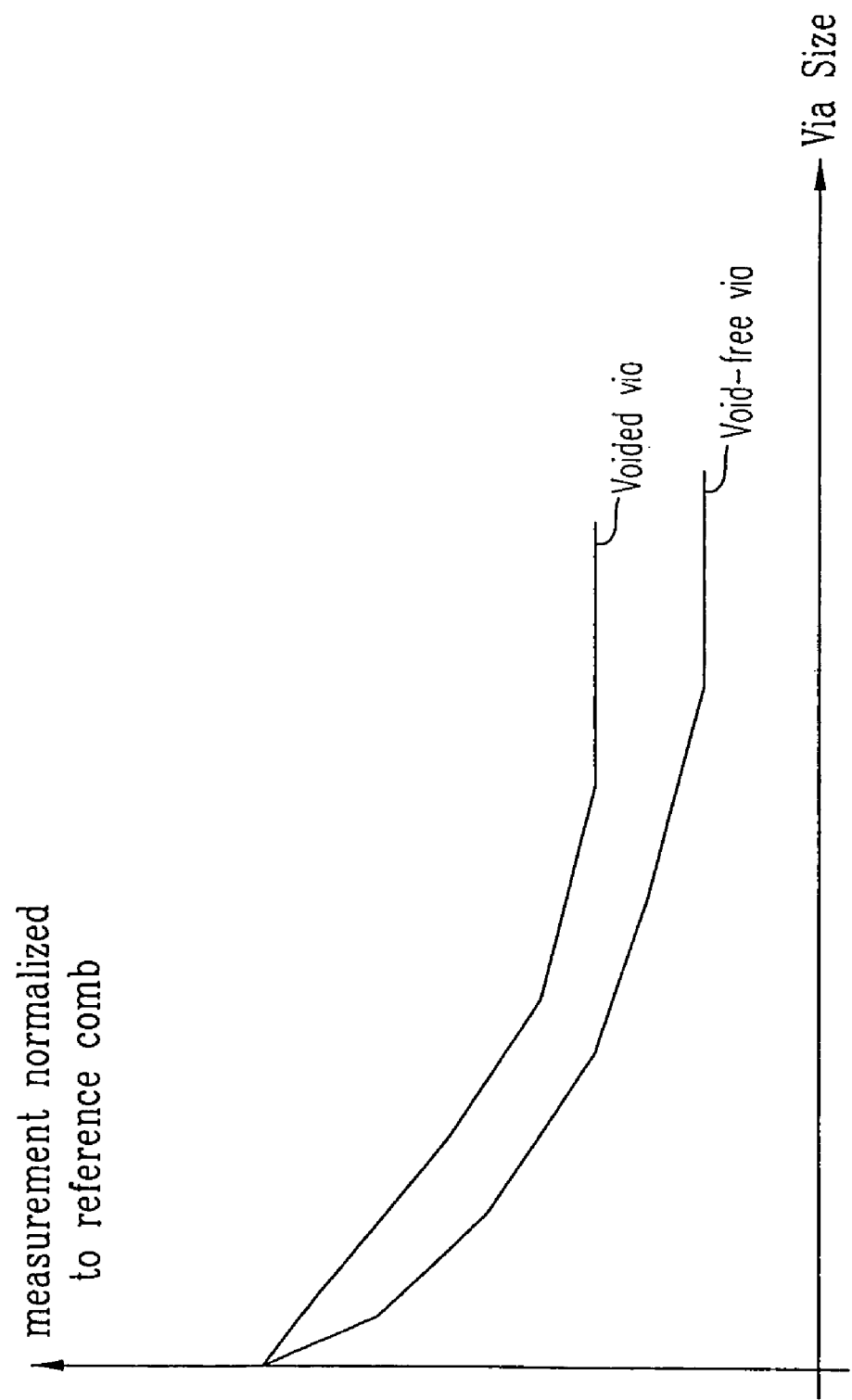
FIG. 2I illustrates, in a graph the difference between measurements of void-free vias and voided vias, as a function of via diameter.

Note that the difference in measurement between voided vias and void-free vias depends on the via diameter as illustrated in FIG. 2I. Specifically, the measurement (when normalized to a region of the comb that is free of voids) reduces as a function of via diameter, but the drop off is greater for void-free vias as compared to voided vias. Therefore, voided vias are easier to detect in a test structure when the via diameter is larger (as compared to a test structure where the via diameter is smaller). As noted above, region 267 in FIG. 2H denotes a conductive region without vias underneath, i.e. a region devoid of a via chain.

Figure 1A:
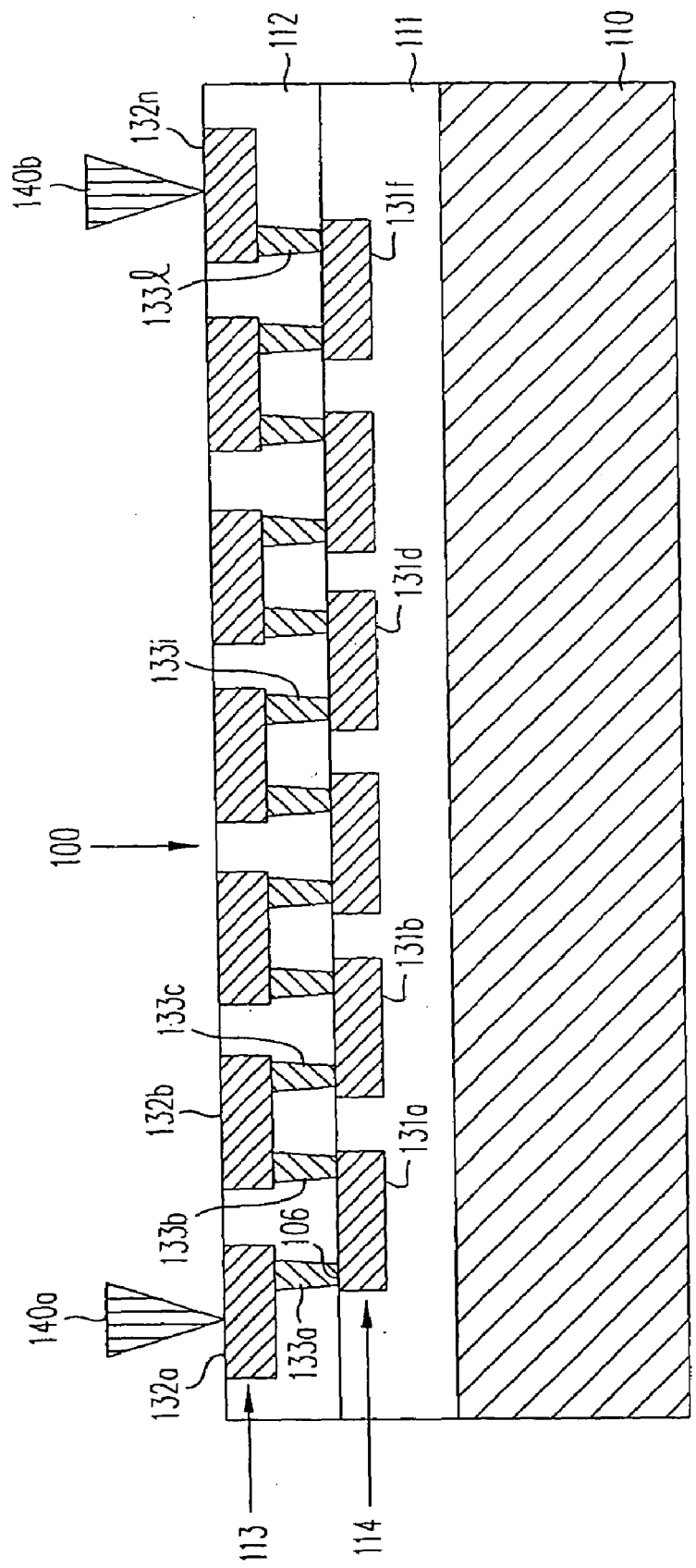
FIG. 1A is a cross-sectional view of a prior art via chain.
Figure 1B:
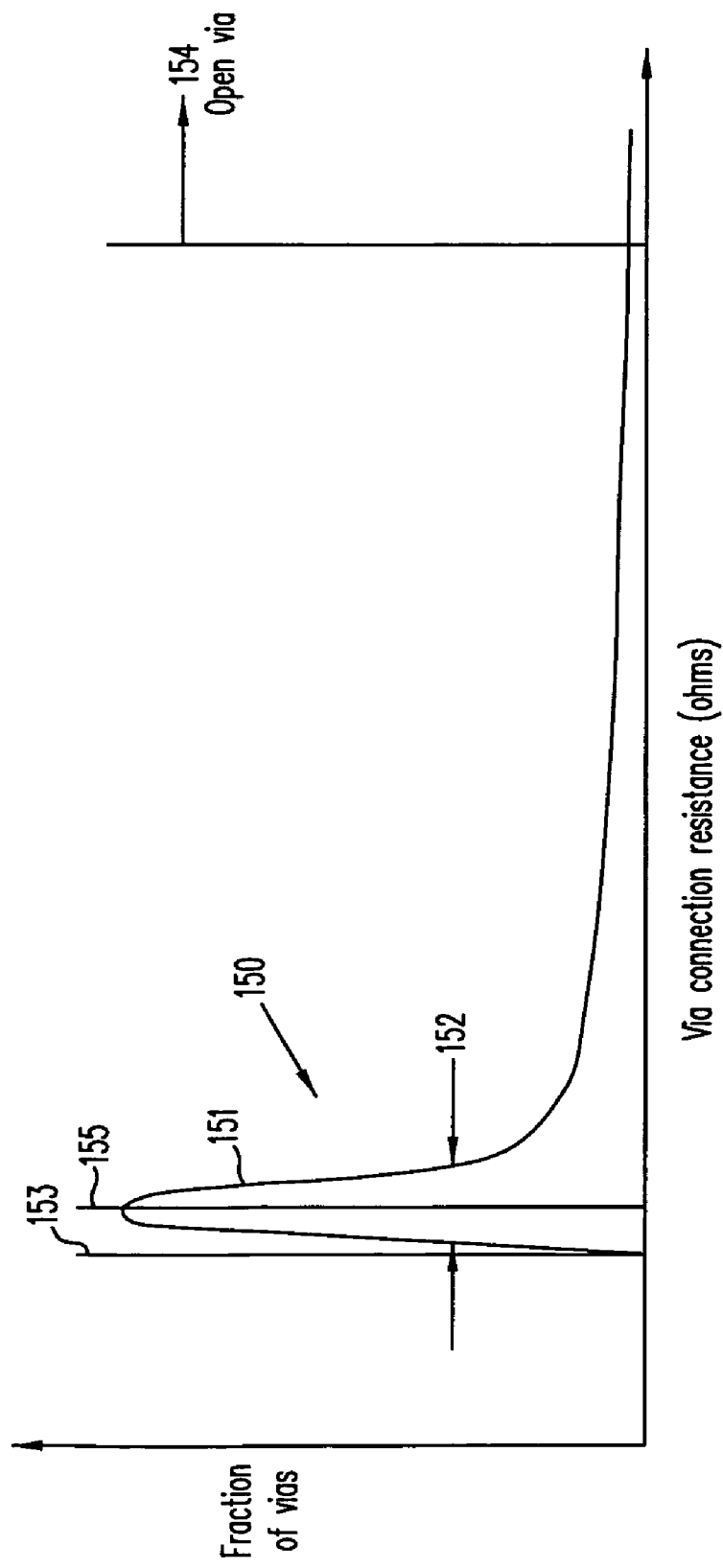
FIG. 1B is a prior art graph showing distribution of resistances of vias.
Figure 2J:
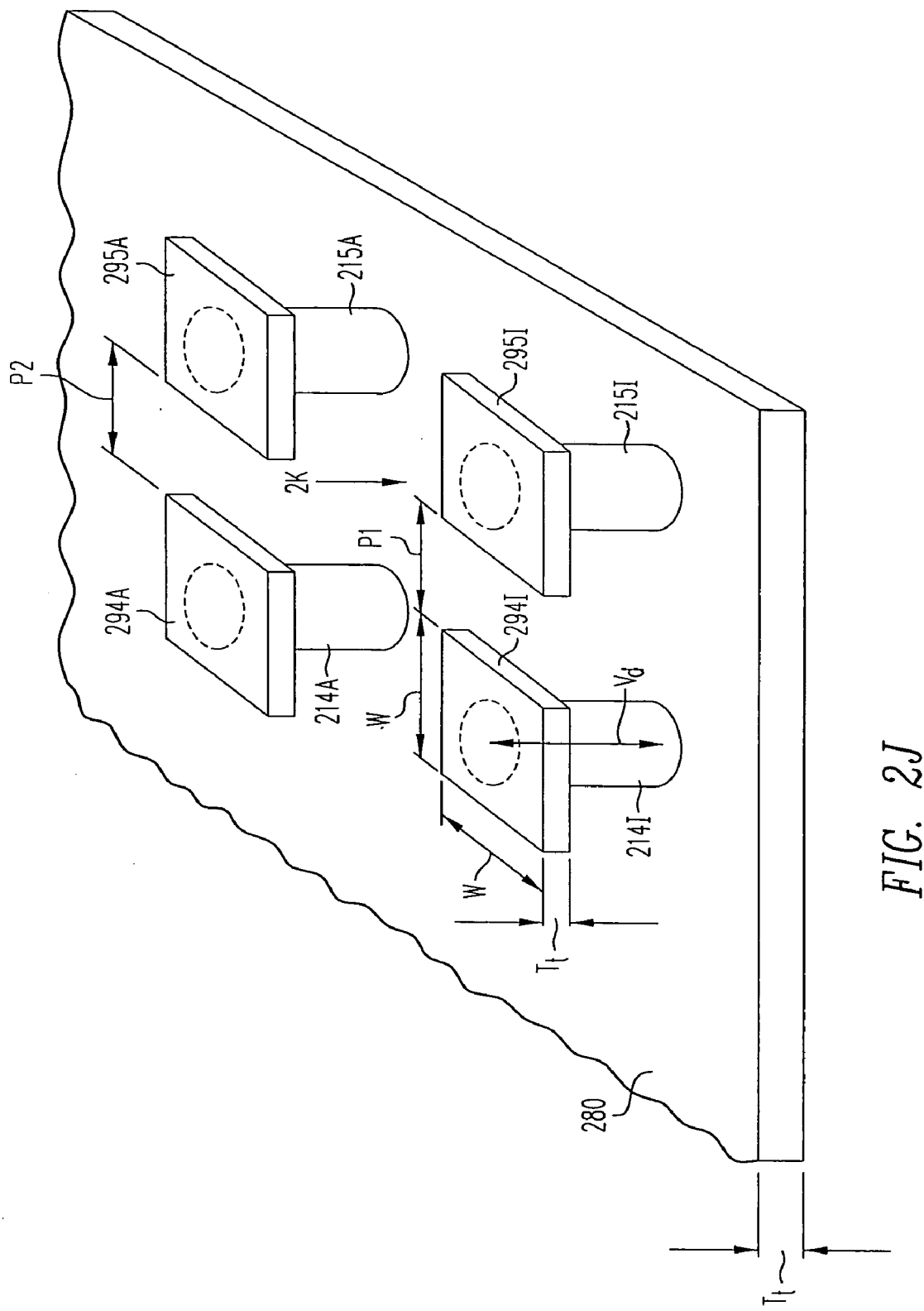
FIG. 2J illustrates, in a perspective view, a test structure in the form of islands of conductive material formed in an upper conductive layer and a sheet of conductive material formed in a lower conductive layer, with the two layers being interconnected by vias.

Also, although an upper layer in conductive structure 210 (FIG. 2A) includes an upper layer of conductive lines each of which is connected to more than one via, in some embodiments the upper layer contains a structure of conductive islands, and each conductive island is connected by only one via to the underlying conductive layer as illustrated in FIG. 2J. Specifically, FIG. 2J illustrates four conductive islands 294A, 294I, 295A and 295I each of which is connected by a single one of the respective vias 214A, 214I, 215A and 215I to the lower layer. Furthermore, in the conductive structure of FIG. 2J, the lower layer includes (instead of lines 222A–222N that are illustrated in FIGS. 2A, 2C and 2D) a continuous sheet of metal (also called "pad") 280 in FIG. 2J Note that heat traveling downwards from island 294I through via 214I into sheet 280 is dissipated in sheet 280 in most embodiments, instead of traveling upwards into an adjacent via, such as via 215I or 214A. This is in contrast to heat transfer in a prior art via chain 100 (FIG. 1A), because the via chain does not have a continuous sheet in layer 114 (heat applied to line segment 132*a* travels downwards through via 133*a*, to the right through line segment 131*a*, upwards through via 133*b*, to the right through line segment 132*b*, downwards through via 133*c* and so on to traverse the length of the via chain.

Figure 2K:
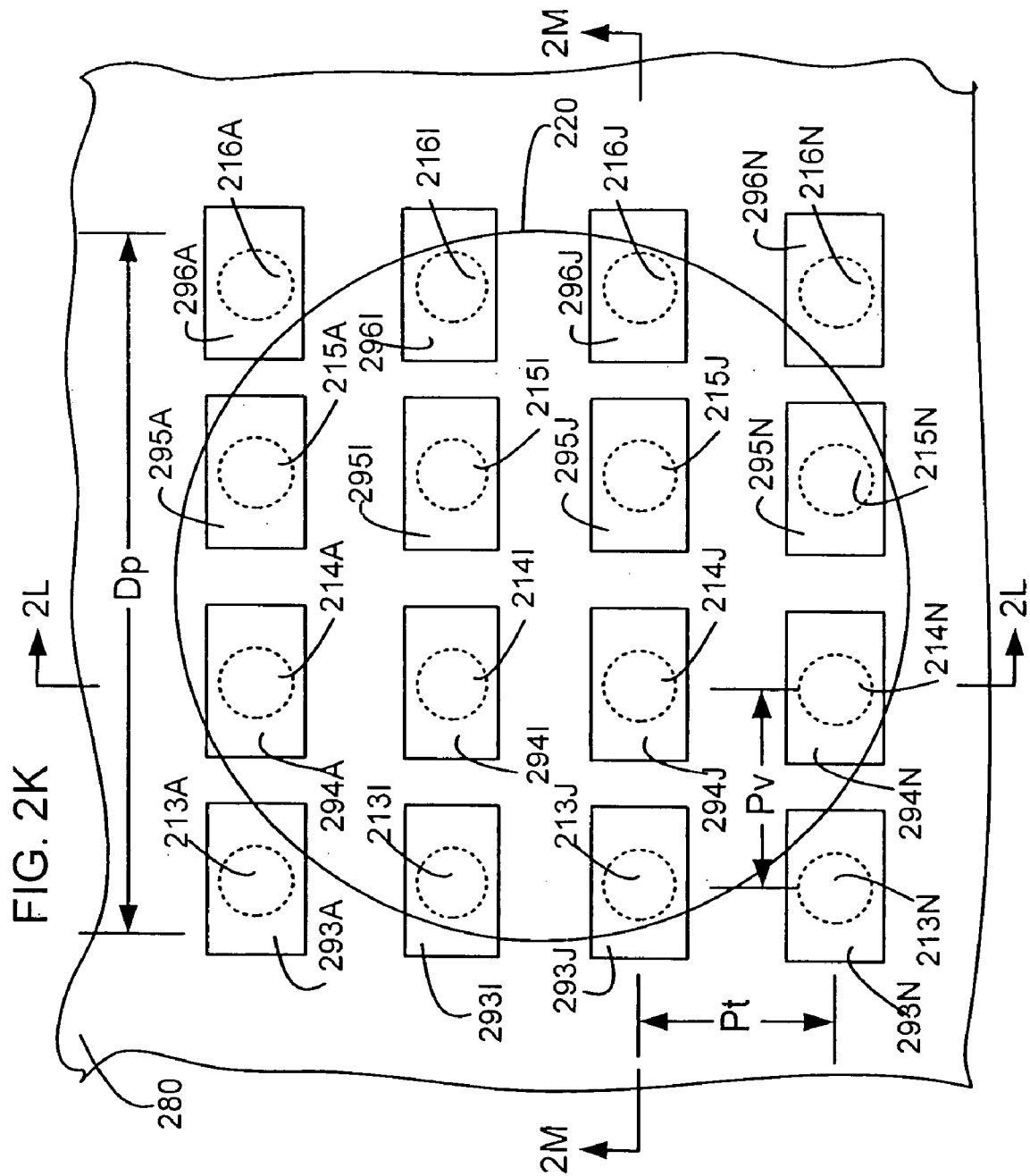

The conductive structure in FIG. 2J is further illustrated in plan view in FIG. 2K, and in two cross-sectional views along the directions 2L—2L in FIG. 2K and 2M—2M in FIG. 2K in the respective FIGS. 2L and 2M. An alternative structure wherein each conductive island is connected by four vias to the lower layer is illustrated in FIG. 2P. For example, in FIG. 2P, conductive island 298A is connected to the underlying layer 280 by four vias 214A, 215A, 214I and 215I.

A conductive structure of the type described in the previous paragraph is formed as a test structure in wafers of some embodiments, to evaluate the efficacy of via formation because a via connection to pad 280 has a greater probability of voiding than a via connection to a conductive line. Note that during evaluation of the type described herein, via 214J of the structure shown in FIGS. 2L and 2M due to being defective causes its respective conductive island (e.g. island 294J in FIG. 2J) to be unable to dissipate heat to any adjacent conductive material in the top layer (by virtue of being isolated therefrom) thereby to rapidly heat up and become more reflective (by an order of magnitude or more) than adjacent islands which are thermally connected to the underlying layer (by their respective vias). In the alternative structure of FIG. 2P, island 298J dissipates heat only through three of the four vias, and therefore heats up (e.g. due to retention of 25% of the incident energy) than an adjacent island, such as island 298A. Also, some embodiments improve detection of via defects by use of a pad as the lower layer (because such a pad is more likely to expose via defects) as discussed below.

In such embodiments, even though an averaged reflectance is being measured by beam(s) 220, the increase in reflectivity of a conductive island is sufficiently high to significantly increase a measurement to a peak of the type illustrated in FIG. 2F. Thus, such a structure of conductive islands provides a higher probability of detecting processes that cause faulty vias. Moreover, another advantage of the conductive island structure of FIG. 2J is that the entire structure (or a large portion thereof) having several islands can be heated simultaneously (as opposed to using a small heating beam that covers only a handful of vias or only one via).

The use of a heating beam (and probe beam if present) which is sufficiently large to cover several tens of vias in many embodiments or even hundreds of vias in some embodiments gives the potential for much greater throughput than the use of beam(s) of sufficiently small diameter to individually resolve each via. Note that the increase in diameter of the heating beam (and probe beam if present) depends on the sensitivity of the measurement to a defect. Several embodiments use the largest diameter beam(s) at which the increase in reflectivity due to a via defect remains noticeable from such a measurement (depending on a given signal to noise ratio).

A typical value for the width "W" in FIG. 2J, is 0.5 μm and the typical diameter of the via is 0.12 μm, and the typical height of the via is 0.3 μm, and the typical thickness Tt of the metal layer is 0.3 μm. In several embodiments, the size of the island (e.g. the diagonal in case of a square island or the diameter in case of a circular island) is selected to be equal to or greater than half the heating beam's wavelength, so as to avoid minimal coupling of the incident light into the structure.

Note that although in some embodiments the islands are located in a regular two dimensional array with equal distance separating adjacent islands from one another, this is not necessarily the case in other embodiments. For example, in the embodiment illustrated in FIG. 2J, the distance P1 between islands 294I and 295I is larger than the corresponding distance P2 between islands 294A and 295A. Note that depending on the embodiment, the islands may be located randomly relative to one another.

Several embodiments take up as much area as possible in the top layer by appropriately increasing the size of the conductive islands (without touching an adjacent conductive island) in order to increase optical coupling with the incident beam(s). Gaps P1 and P2 (FIG. 2J) between the conductive islands are selected to be significantly smaller than the incident beam(s) wavelength—0.2 μm or less—so as to minimize leakthrough of light to the underlying structure (which can reduce effectiveness of such measurements in detecting via defects).

Figure 2N:
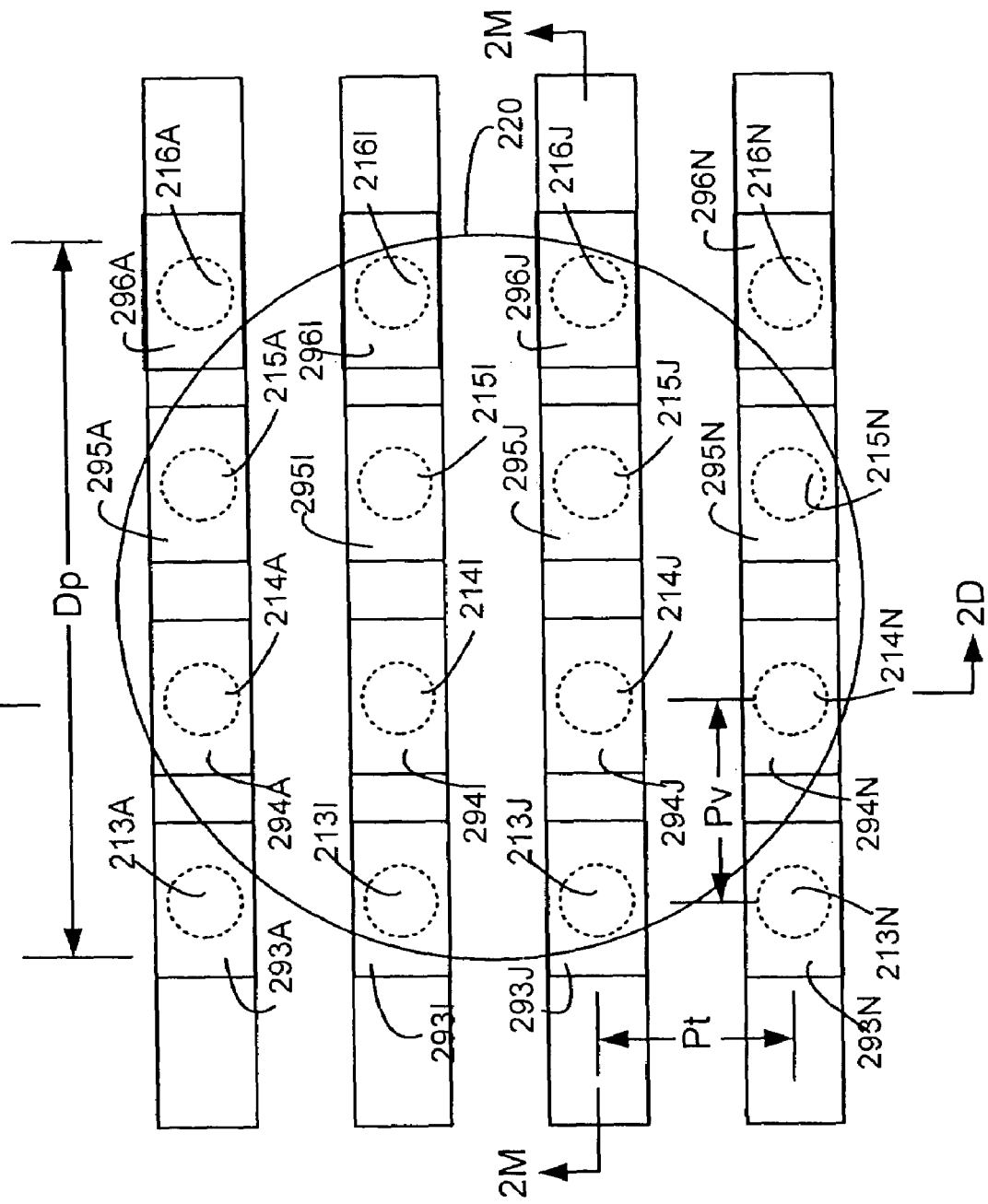
FIG. 2N illustrates, in a plan view, a structure similar to the structure in FIG. 2J in the form of islands of conductive material formed in the upper conductive layer but with lines of conductive material formed in the lower conductive layer, with the two layers being interconnected by vias.
Figure 2P:
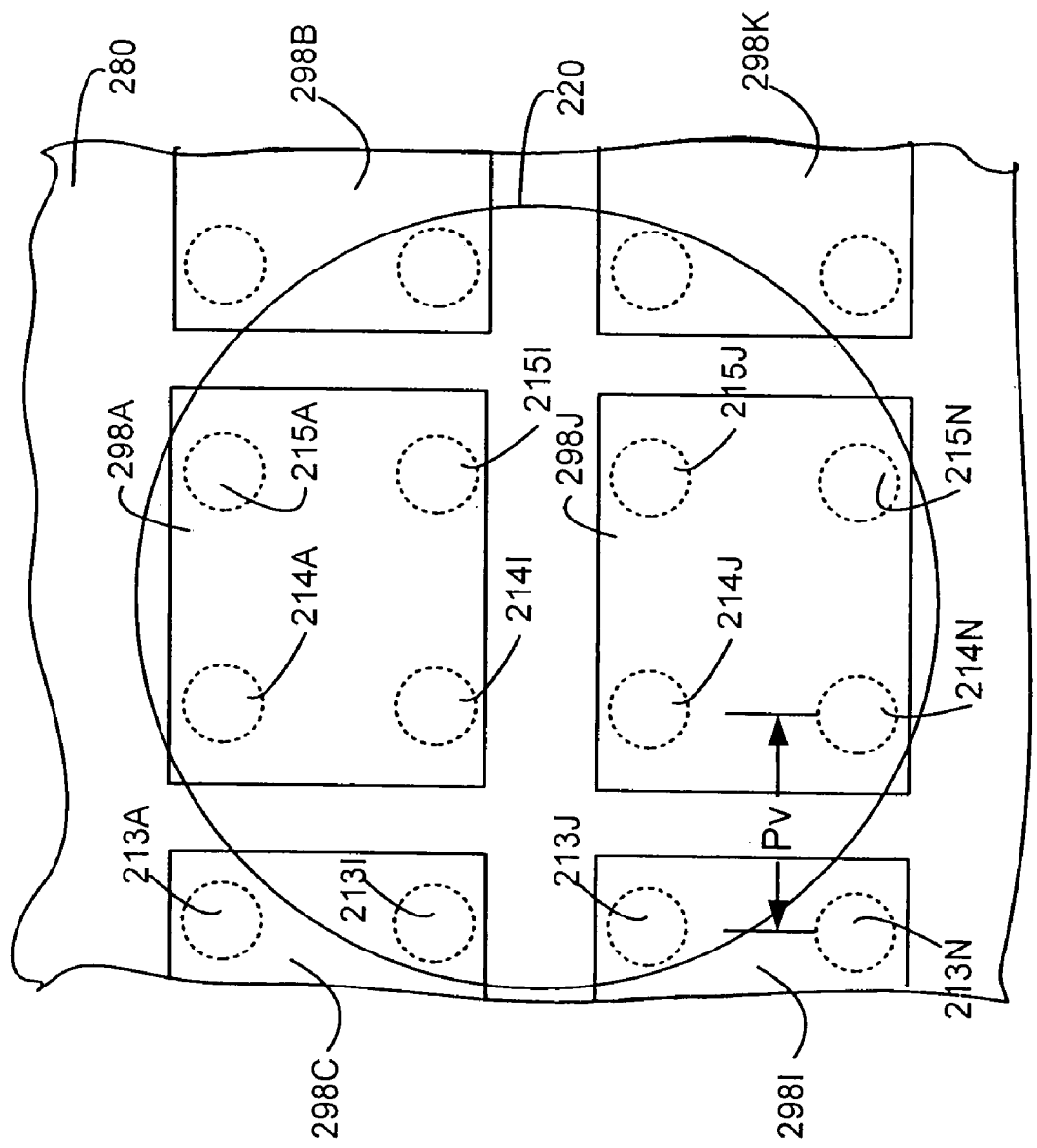
FIG. 2P illustrates, in a plan view, a test structure of the type shown in FIG. 2K but with each island in the upper layer being interconnected to the underlying layer by a small number of vias (e.g. four vias) instead of a single via per island as shown in FIG. 2K.

Furthermore, although in some embodiments the lower layer of conductive material is formed as a sheet as illustrated in FIG. 2J, a similar test structure may be formed with the lower layer formed as an array of conductive lines as illustrated in FIG. 2N. In such embodiments, the cross-sectional view in the direction 2D—2D (see FIG. 2N) appears similar or identical to FIG. 2D, whereas the cross-sectional view in the direction 2M—2M (FIG. 2N) appears similar or identical to FIG. 2M. The conductive pad of FIG. 2J is believed to be superior to the conductive lines of FIG. 2N because of the greater likelihood of a via failure when the connection is to an underlying pad (than to a conductive line). Therefore, a structure with the lower layer being a sheet enhances the sensitivity of a method of the type described herein to the possibility of via failure.

Moreover, as will be apparent to the skilled artisan, although a comb structure was described as being used in some embodiments (see FIG. 2A), a serpentine may be used in other embodiments (see FIG. 2O).

Whether or not a measurement of the type described herein is effective in determining the average resistance Savg of vias underneath a conductive island (of the type shown in FIG. 2P), and of detecting an increase in resistance due to one or more via defects therein, depends not only on the number of vias underneath each island, but also on other factors, such as diameter Dp of the illuminated area, and minimum geometry (e.g. via diameter).

In many embodiments, a dimension of the conductive islands (e.g. diameter of circular islands or diagonal of square islands) is selected based on the diameter Dp of the area being illuminated (by the probe beam and/or heating beam). In certain embodiments, the island dimension is chosen to be no more than 2*Rt where Rt is the distance from the center of the illuminated area at which the temperature rise is less than 10% of the maximum temperature rise (at the center of the illuminated area) under ideal conditions.

In an example of the just-described embodiments, diameter Dp is 2 μm and via diameter is 0.5 μm and Rt is 4 μm (which is typical), and hence conductive islands are formed to be squares of width no larger than 8 μm. Note that distance Rt depends on a number of factors, such as the thermal conductivity of the material of the conductive islands, thickness of the conductive islands, and thermal conductivity of a layer (e.g. of dielectric) that is located immediately underneath and in contact with the conductive islands.

Note that conductive islands (of the type illustrated in FIG. 2P) can be made of a dimension smaller than 2*Rp, depending on the embodiment. In some embodiments, each conductive island has only one via (or a small number of vias, e.g. 12 vias), while the probe and/or heating beam illuminates a large number of islands, such as 100 islands or 300 islands. Note that in such an embodiment, a single measurement covers all the islands that are illuminated, without resolving the contribution of individual islands.

When the number of measurements (e.g. 2500) is sufficiently large, they are used in some embodiments for statistical analysis that may be performed as discussed next (instead of or in addition to the above-described moving average analysis). Specifically, after all measurements are made over an array of conductive lines, the measurements are analyzed as per act 303 (FIG. 3A) to see if a statistical evaluation of the measurements indicates that the wafer is acceptable and if so the wafer is processed further (as per act 305) and if not the process parameters are changed (as per act 304).

In one embodiment of act 303, any measurement that deviates from an average (e.g. statistical mean, or median or mode) in a significant manner is deemed to be sufficient to indicate that the wafer is unacceptable. Specifically, if a significant deviation is found during statistical analysis, then the array is marked as having defective vias, and a process parameter that is used in fabrication of the array is changed (as per act 304).

Depending on the embodiment, any of a number of different methods of identifying a significant deviation in the measurements may be used. Specifically, in some embodiments, any measurement that happens to be greater than the average by more than three times the standard deviation (i.e. >3σ) is deemed to indicate the existence of one or more partially conductive vias in the area being evaluated. In such embodiments, at most 1% of measurements containing all good vias are likely to exceed this boundary (e.g. because 99% of all measurements fit within ±3σ of the average). The standard deviation σ may be computed in the normal manner, as shown below:

$$\mathrm{sqrt}((\Sigma(X_i - X)^2/(n-1)) \text{ where:}$$

sqrt=square root;
Σ=summation;
Xi=measured signal;
X=mean of all measured signals; and
n=number of measurements.

Figure 3A:
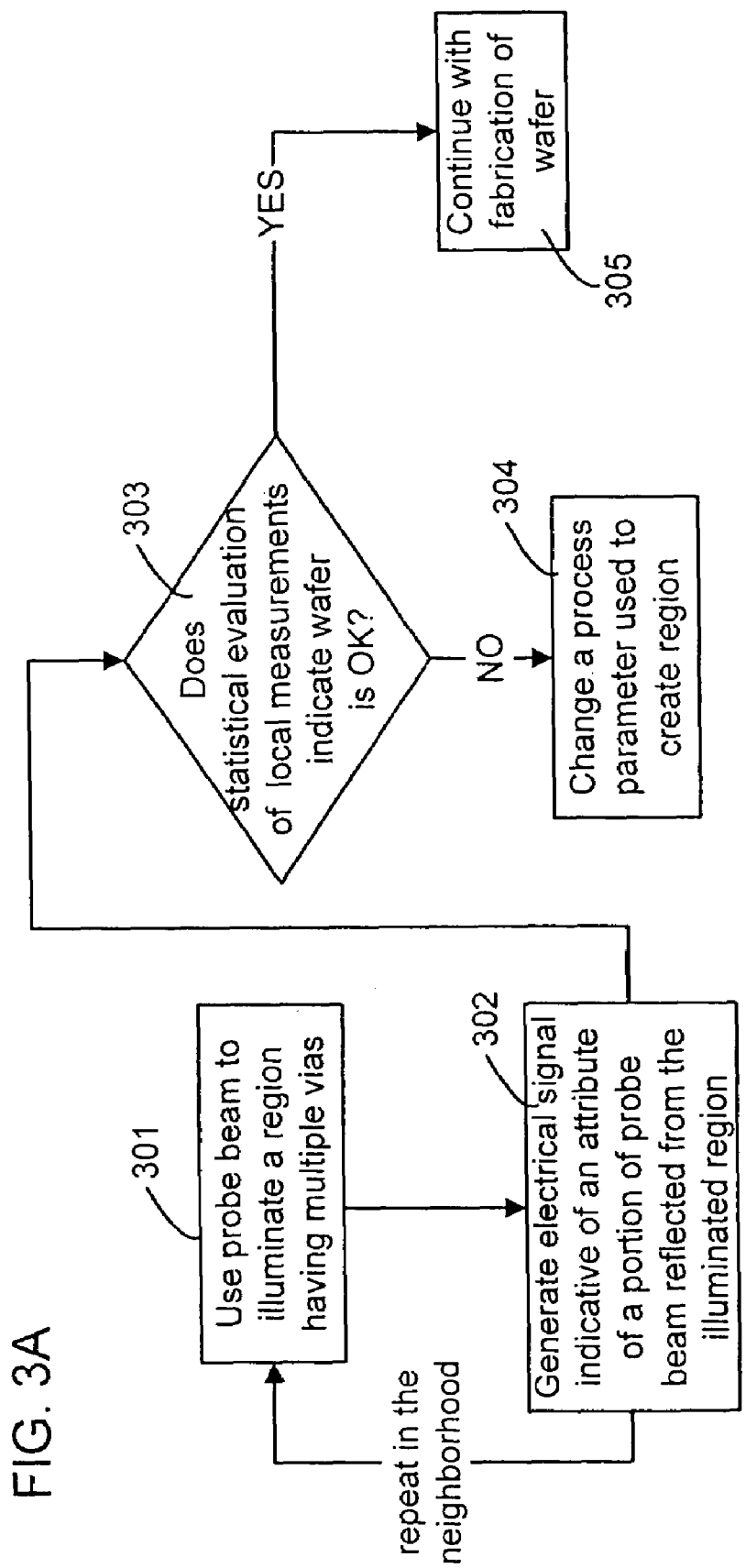
FIG. 3A illustrates, in a flowchart, acts performed in accordance with an embodiment of the type illustrated in FIGS. 2A–2D.
Figure 3B:
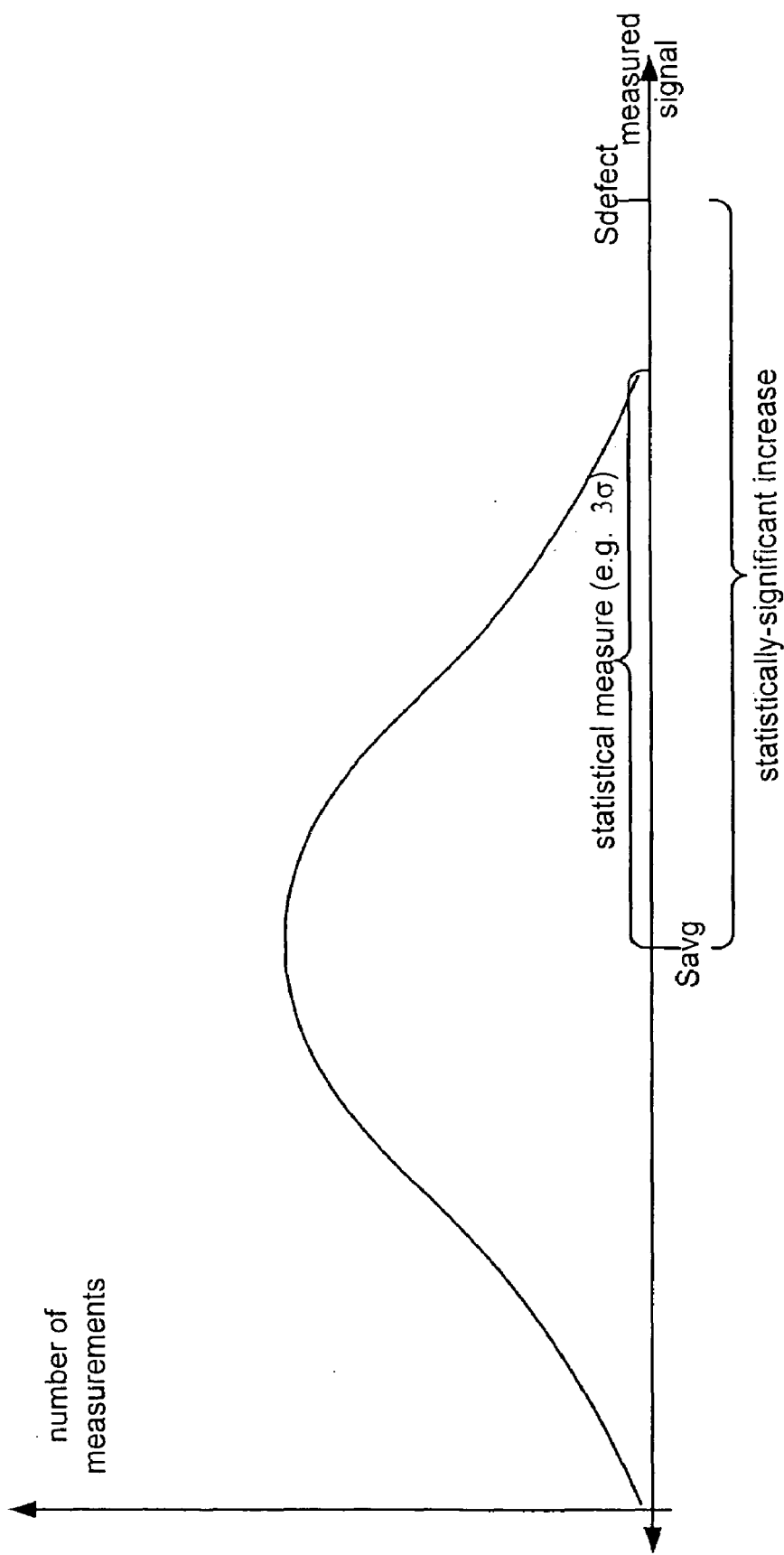
FIG. 3B illustrates, in a graph, a statistical plot of the measurements made by the method of FIG. 3A, to illustrate a statistically significant deviation in the measurement indicative of a defective via.

As illustrated in FIG. 3B, any increase that exceeds an average measurement Savg by three sigma is deemed to be statistically significant and indicative of a partially conductive via in some embodiments. In other embodiments, a larger limit is used to decide whether a measurement is indicative of a partially-conductive via, e.g. four sigma greater than Savg.

In several embodiments, smaller limits (e.g. 2σ or even σ greater than the average Savg) are used e.g. if a wafer fabrication process is known to fabricate wafers with a small number of via defects. Moreover, although a statistical measure is used as a limit in some embodiments, other embodiments may set a non-statistical limit on the signal being measured, based on calibration with wafers that are tested and found to be good. For example, inclusion of a single partially conductive via in a measurement may cause the measurement to become two (or more) times greater than the corresponding measurement obtained when all vias that are included in the measurement are fully conductive. In such a case, as soon as a measurement exceeds the average by 50% the region under evaluation may be deemed to contain one or more partially conductive vias.

Although in some embodiments several thousand measurements (e.g. 2500) are performed and then statistically analyzed, the number of measurements that are sufficient for such statistical analysis is much smaller (and the smaller number is used in other embodiments). For example, only 100 measurements may be performed in certain embodiments, and these 100 measurements are statistically analyzed, although it is quite possible to make (and use) only 30 measurements (with each measurement covering 10s of vias or 100s of vias). Note that measurement and evaluation of fewer than 10 measurements is unlikely to yield a result that is statistically meaningful because each measurement forms 10% of the sampling. Moreover, the results are also not meaningful in such situations if each measurement covers too small of a fraction of the array area. However, when problems are anticipated that cover larger areas, such as etch non-uniformity, then such sampling may be acceptable, depending on the embodiment.

Moreover, in many embodiments, all of the measurements that are statistically analyzed are from a single localized area (e.g. from a region containing an array of conductive lines within a die or a street between two dice), so that non-uniformities across the wafer do not affect the result of analysis. Such measurements may be repeatedly made in several localized areas across the wafer area to map uniformity across the wafer. In some embodiments, all arrays on the wafer are checked for conformance to the same control limits. Moreover, measurements of the type described herein may be made at any metal level (M1 to M2 vias, M2 to M3, etc. In such a case, measurements in an upper-most pair of metal layers may be affected by structures (and/or defects) in metal layers underneath thereof. In such embodiments, the control limits may be corrected to account for presence of such underlayers. Moreover, such measurements may also be made through an overlaying dielectric film, which may similarly (or equally) affect the amplitude of the response of all measurements.

Figure 4A:
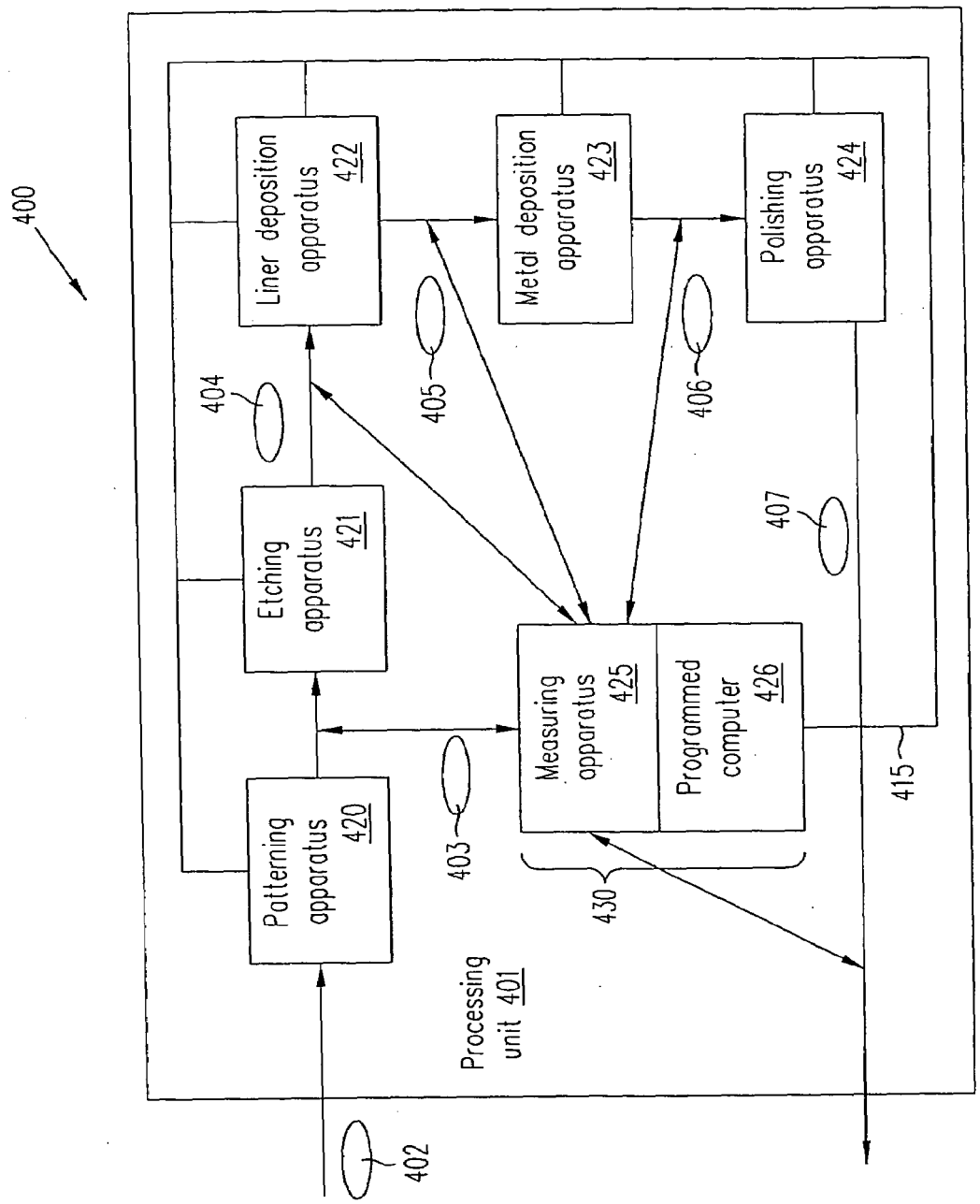
FIG. 4A illustrates, in a block diagram, an apparatus used with the method of FIGS. 2A–2D in one specific implementation.
Figure 4B:
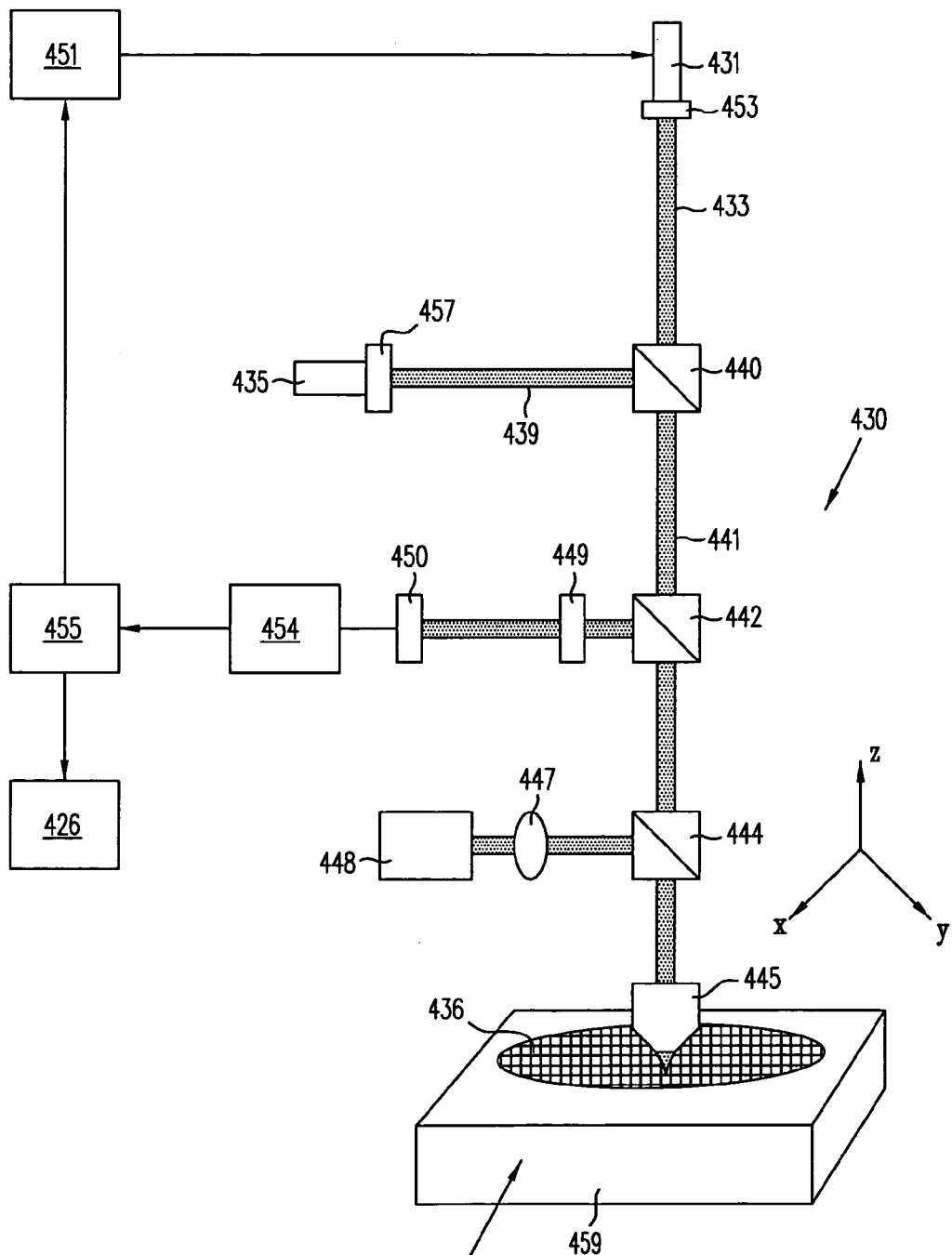
FIG. 4B illustrates, in a block diagram, an apparatus used with a method of the type illustrated in FIG. 3A, in one specific implementation.

As illustrated in FIG. 4A, a processing unit 400 of one embodiment that implements a method of the type described herein includes a measuring apparatus 425 (FIG. 4B) that performs the process described above. Therefore, at any point during wafer fabrication, a wafer can be subjected to the measurement process e.g., as illustrated by arrows 310-314 in FIG. 3A. If a measured signal exceeds a predetermined limit, the fabrication process can be adjusted in real time, thereby to produce more wafers that are acceptable (than if measurements were done after wafers are fabricated).

One embodiment of processing unit 400 includes an optional programmed computer 426 that supplies a process parameter (used in the fabrication process) on a bus 415 that is coupled to each of patterning apparatus 420, etching apparatus 421, liner deposition apparatus 422, metal deposition apparatus 423, and polishing apparatus 424. A change in the process parameter that is to be made can be determined automatically by software in programmed computer 426, or can be entered by a human operator.

In one embodiment, a single measurement from wafer 407 of the type described herein is sufficient to identify the presence or absence of a partially conductive via when the measurement is compared with a corresponding measurement from another wafer (such as the wafer that was fabricated immediately prior to the wafer currently being evaluated). In one embodiment, error due to variation in the width of a metal line is eliminated by comparison of a measurement of the type described herein with a corresponding measurement from a conductive structure (comb, serpentine or via chain) that is devoid of vias.

FIG. 4B shows a representative measurement apparatus 430 using a laser 431 to heat the conductive structure in wafer 436 and a second laser 435 to measure temperature of the heated region. However, alternate apparatuses are equally viable. For example, an electron or ion beam can be used to heat a conductive structure in wafer 436 and an infrared camera or detector (e.g. thermal imaging detector) can be used to measure the blackbody temperature of the conductive structure.

In one specific embodiment of apparatus 430, laser 431 is a diode laser (e.g. made by Spectra Diode Labs of San Jose, Calif., USA), emitting a beam of intensity 100 mW at a wavelength of 830 nm. A laser driver 451 (e.g. Part number 8000 OOPT-42-12-02-NN available from Newport Corporation, Irvine, Calif., USA) provides a sinusoidal signal to laser 451, thereby to modulate the intensity of a heating beam generated therefrom. Optics 453 (e.g. Part number C390TM B, Thor Labs, Newton, N.J., USA) collimate the output of laser 431, creating beam 433.

In one embodiment, heating beam 433 is unpolarized, while in another embodiment, heating beam 433 is polarized. Specifically, in certain embodiments, when the line width is less than 0.2 mm, heating beam 433 is polarized. The polarization direction is oriented parallel to the length of a via chain in structure 210, to increase heat absorption, e.g. due to interaction between heating beam 433 and the metal line segments (also called traces) in structure 210. As noted above, structure 210 is formed within wafer 436.

As noted elsewhere herein, certain embodiments use one or more polarized beams when the line width is less than the wavelength. In such embodiments, light polarized parallel to a conductive line (also called "trace") has a larger interaction cross-section than light polarized perpendicular to the conductive line. Use of one or more parallel polarized beams (either as a heating beam or as a probe beam or both beams may be polarized) increases the efficiency of evaluating structure 210 and therefore increases the signal-to-noise ratio (SNR) of the measured signal.

Laser 435 which is also included in apparatus 430 as one embodiment may be made by Spectra Diode Labs, and emits a beam of intensity 50 mW at a wavelength of 980 nm. Laser 435 generates probe beam 439 at a constant intensity. Depending on the embodiment, probe beam 439 may also be polarized, parallel to the length of the via chain. Optics 437 (e.g. Part number F230FC B, Thor Labs, Newton, N.J., USA) collimate the output of laser 435 to create probe beam 439.

Apparatus 430 also includes a dichroic mirror 431 (e.g. Part number O5BR08 available from Newport Corp.) that transmits light from laser 431 and reflects light from laser 435 (which is of longer wavelength than light from 431). Dichroic mirror 440 combines beams 433 and 439, providing single combined beam 441. Combined beam 441 passes through various optics and is ultimately focused on wafer 456 with objective lens 445, which is e.g. a 100×0.9 NA lens (such as Part number 1 LM5951) from Olympus of Tokyo, Japan.

The beams reflected by wafer 446 pass back to a 50:50 beam splitter 442, which diverts 50% of the return beams toward detector 450 (such as silicon PIN photodiode, e.g. Part number S2386 8K from Hamamatsu Corporation, Bridgewater, N.J., USA) through filter 449. Filter 449, which may be a GaAs wafer, removes the reflected portion of light from heating beam 1303, so that the detector sees only light from probe beam 439. Trans-impedance amplifier 454 converts an electrical signal output by detector 450 to a voltage, which is measured using a lock-in amplifier 455 (such as SDP lock-in amplifier, e.g. Part number 7265 available from EG&G Instruments, Atlanta, Ga.). Lock-in amplifier 455 has an oscillator that is also used to drive the modulation of laser driver 451. The oscillator is operated at a frequency on the order of 2 kHz or lower.

In one embodiment, the oscillator frequency (which is used to generate a heating beam) is selected to be sufficiently low to prevent a majority of the applied heat from forming a thermal wave, i.e. causing the temperature distribution in a via chain structure at any instant (e.g. over the duration of a single cycle of modulation, e.g. over 500 μsec for 2 KHz modulation) to approximate the instantaneous temperature that would be normally seen in steady state (e.g. see the linear response conditions discussed in U.S. Pat. No. 6,054,868, which patent is incorporated by reference herein in its entirety).

In other embodiments, the modulation frequency may be selected to be large enough to cause a portion of the energy from heating beam 433 to be converted into a thermal wave, while the remaining energy of beam 433 is sufficient to cause the reflected portion of probe beam 439 to be modulated at the modulation frequency when a via chain (or other feature is being evaluated) in structure 210 is not defective. Therefore, a method of the type illustrated in FIG. 2A is used in accordance with the invention to further process a wafer if the measured signal is within a predetermined range of a corresponding signal from a reference wafer (regardless of the presence or absence of a thermal wave depending on the embodiment).

Regardless of the frequency selected, the use of a modulated heating beam as described herein enables use of a lock-in amplifier to obtain a very sensitive measurement of small temperature changes. Note, however, that in other embodiments, the heating beam 433 may be of constant intensity (i.e. no modulation) as long as the reflectance of the conductive structure 210 is measured with sufficient accuracy (e.g. 1%). A thermal imager may be used instead of detector 450, to perform such a constant intensity measurement.

As noted above, the reflectance of the conductive structure 210 that is being heated by a modulated heating beam 433 in several embodiments of the invention cycles approximately in phase with modulation of the heating beam 433. This is because the reflectance of a metal is a function of temperature. Copper, for example, has a coefficient of reflectance change of $-1.55 \times 10^{-5}$/° C. (about 15 parts per million). The phase of the measured signal depends on the conductive material used to form the structure 210, e.g. since the reflectance of copper decreases with increasing temperature, the reflected signal is approximately 180 degrees out of phase for this metal, depending on the amplitude of variation in temperature.

Note that the amount of phase change depends on the composition of the conductive material that is used to form vias and traces in the conductive structure 210 (in addition to depending on the change in temperature). The amount of heat being applied may be selected to ensure that the changing reflectance of the conductive structure 210 due to temperature change causes a modulation signal in the reflected portion of the probe beam 439 (e.g. in embodiments that modulate the intensity and/or the polarization of a heating beam). This is the signal measured by the lock-in amplifier 455. The intensity of the measured signal is therefore a function of the temperature of the via chain at the measurement point.

The apparatus 430 illustrated in FIG. 4B also includes a vision system to enable location of the laser beams 433 and 439 on the via chain in structure 210 in wafer 436. Beam splitter 444 diverts approximately 10% of the reflected light to lens 447 and camera 448. In this embodiment, objective lens 445 and lens 447 form a microscope with a magnification of approximately 1000×. Camera 448 of apparatus 430 is connected to an external vision system (e.g. Patmax from Cognex, Inc. of Boston, Mass.). The vision system in turn is connected to a wafer stage 469 in apparatus 430 to enable automatic alignment of the laser beams 433 and 439 to the via chain structure 210. Apparatus 430 also includes a white-light illuminator (not shown) to provide illumination for the vision system.

In one example, wafer 436 is in production and requires a level of metal interconnection (also called interconnect layer). During the fabrication process, wafer 436 is transferred into process module 400 (FIG. 4A) where the just-described interconnect layer is formed thereon (and this wafer is now labeled as 406 and is to be evaluated).

Module 423 (FIG. 4A) may create one or more voids when creating the interconnect layer in wafer 406, depending on the process being used. For example, electroplated copper is the metal of choice for dual damascene interconnect devices. However, the process of creating copper metal trenches and vias leaves the conductive structures being formed vulnerable to voids.

After the diffusion barrier (typically Ta or TaN) is deposited, a thin copper seed is deposited by physical vapor deposition (PVD) to ensure equal potential across all features for electron transfer between the plating bath used to deposit the electroplated copper. If the PVD copper seed layer is too thin or does not cover all the features in trenches or vias, electroplated copper will preferentially plate on areas covered with copper, resulting in no deposition, or voids, on the areas with little or no copper seed.

Because of the line-of-sight nature of PVD, narrow device features such as trenches that have high aspect ratios are prone to little or no copper seed deposition on the sidewalls, which results in "sidewall" voids. Any "shadowing" feature in a trench or via that blocks the PVD line-of-sight will result in lack of copper seed coverage, also resulting in a void.

A non-optimized concentration of accelerator in the plating solution can lead to "seam" voids in a conductive structure and such voids can be detected by the method of FIG. 3A. The correct concentration of accelerator species in the bottom of trenches and vias enhances "bottom up" electroplated copper fill. If the concentration of accelerator in the plating solution is too low or too high, the deposition rate in the bottom of the features approaches that of the sidewalls and top, resulting in conformal copper deposition. This conformal deposition coupled with non-conformal cusping of PVD coverage at the top of device features forces closure of the top of the feature before trenches or vias are completely filled, resulting in a seam void.

There are several other mechanisms for void creation, such as etch residues at the bottom of a small hole, poor adhesion of a via copper plug or trench copper line to the underlying barrier metal, void agglomeration due to copper recrystallization, and electromigration. Voids created by any of these mechanisms are detected by the method of FIG. 3A.

The method of FIG. 3A also detects other defects, such as a poor connection at the bottom of a via, or poor plating that may be caused by, for example, presence of residue from an etch process used to etch a hole in the dielectric layer in which a via is formed. In the just-described example, instead of residue, the etch process may be incomplete and therefore cause poor connection or poor plating at the bottom of the via.

In addition, an integrated circuit contains several interconnect layers. Formation of such a layer of an integrated circuit requires exposure to temperatures of several hundred degrees Centigrade during the deposition of the dielectric layer. Exposure to such high temperatures can cause an otherwise good via to pull back (either partially or completely) at the bottom of the via hole, resulting in a partial or open connection with the underlying trace. Also, etch residues can corrode the connection at the bottom of the via during such high-temperature exposure. In some of these cases, the via may partially connect, but its resistance increases, for example, from 1 ohm for a good via to 10 ohms for a via that is only 10% connected. Such problems may be isolated and therefore undetectable using conventional methods such as electrical testing of a via chain, which only provides the average resistance of a large number of vias.

However, such problems are believed to be within the resolution of several embodiments of the present invention, and the problematic vias may appear in a map of a via chain area of the type described herein These types of voids are buried, and hence invisible from the top of the integrated circuit. In addition, the voided or partially filled vias are buried under dielectric layers. Thus, a method of the type described above in reference to FIG. 3A is particularly advantageous in such a situation because the method measures degree of voiding, as opposed to just identifying whether a via is connected or open. Moreover, a method in accordance with the invention can be used after transparent dielectric layers have been applied to bury the via structures, so that no metal is exposed at the top surface.

Wafer 406, with a completed interconnect layer, possibly having one or more voids, is measured in system 425 to determine if vias have been successfully formed. Measurement can be in selected areas of the active device pattern, or in a test structure adjacent to the active device pattern. Measurement signals generated by system 425 are transferred to a computer 426. In the event that results are judged unacceptable (for example, because a strong signal is detected), signals are sent by computer 426 to process module 423 to alter the process to enable correction of the detected problem. Alternatively, computer 426 may simply cause the process module 423 to halt, thereby to prevent production of additional defective wafers. A human operator may restart module 423 after correcting a via voiding problem.

Figure 4C:
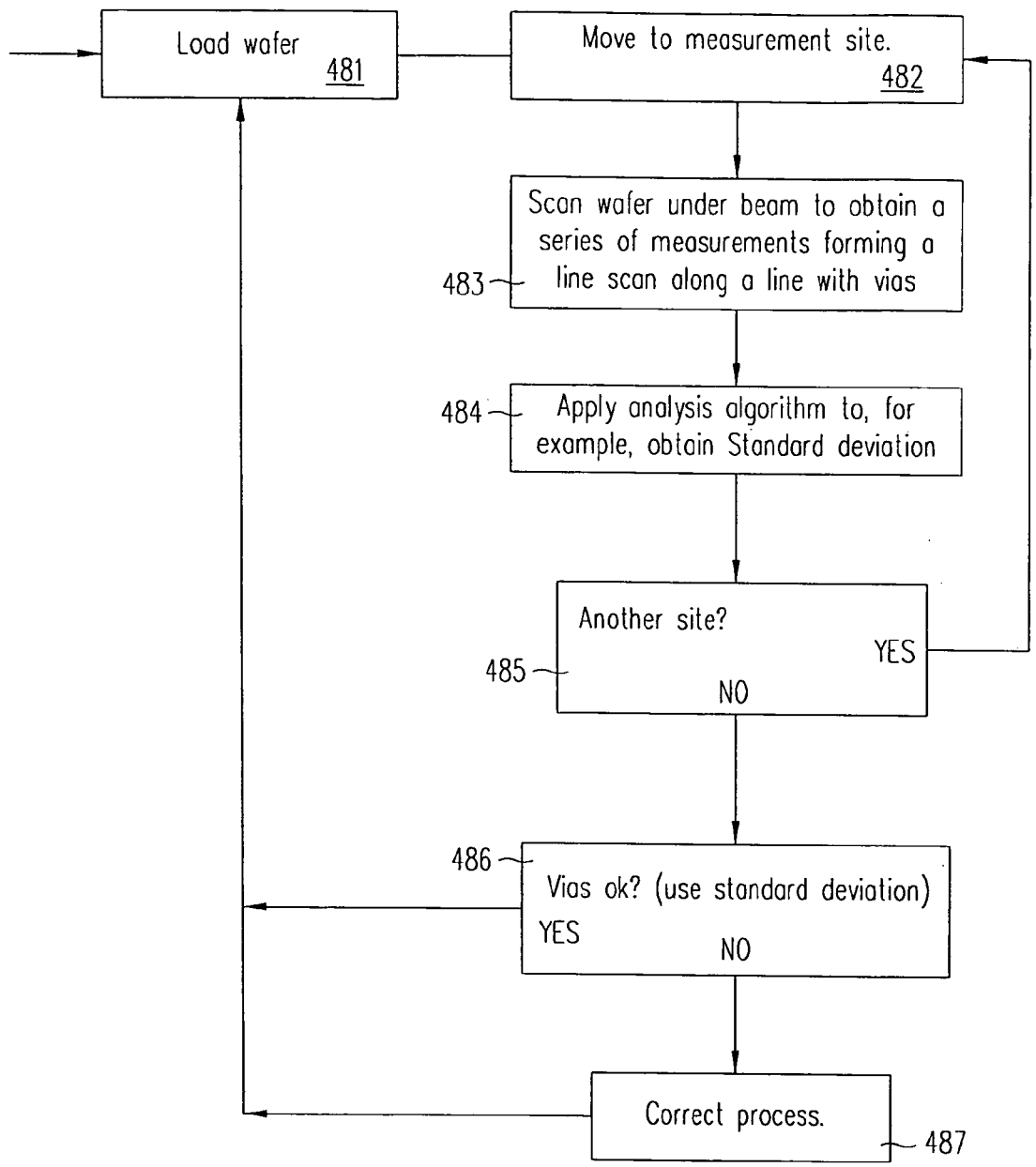
FIG. 4C illustrates, in a flowchart, acts performed by the system of FIG. 4B in one embodiment.

FIG. 4C shows a flow chart associated with measurements that are performed by apparatus 425 and computer 426 in one specific embodiment. In act 481 a wafer 406 is loaded into the measurement system 470 (FIG. 4B). In act 482 the wafer 406 is moved to a position so that a scan can be made along a via chain (this position is also called the measurement site). The beams 433 and 441 are both focused onto the measurement site during act 482.

A loop of acts 483–485 is now entered to perform measurements. A line scan along the conductive line(s) is performed in act 483 as described above. Specifically, the line scan consists of a sequence of taking a measurement, translating the wafer a small distance typically along a straight line (in one example less than the diameter of probe beam 489) so that the feature under measurement is translated under the beam and a new measurement site is illuminated by beam 489, taking a measurement at the new measurement site, and repeating these acts. As described earlier, the scan may be stopped periodically to verify that the beam is properly positioned on the via chain and to adjust the positioning as required.

In one embodiment, the measurement sites are evenly spaced by a distance smaller than the beam diameter. For example, steps of 1 µm may be made with probe beam of diameter 2 µm. In one specific implementation of such a scan, the stepping distance is less than the beam diameter, in order to provide a plot of a continuous signal from the scan. In another embodiment, the location of each via is a measurement site, although one or more non-via locations between two vias may also be used as measurement sites.

In another embodiment, the beams are continuously scanned with respect to the wafer, either by moving the stage or by scanning the beams. The signal is integrated over the time taken to scan the distance of one pixel and read out. For example, at a scan rate of 200 µm/sec, with a pixel size of 2 µm, the signal is read every 10 msec. In another embodiment, the heating beam is a ribbon and the probe beam is scanned within the ribbon. In one embodiment, the wafer is moved under the ribbon. In another embodiment, the ribbon is scanned along a feature of interest.

In step 484 the set of measurement signals is analyzed, for example, by computing the standard deviation of the set of measurement signals (which have discrete values, one for each measurement site or, alternatively, with a continuous scan with a value output by the lock-in amplifier during a scan). A measurement signal that is significantly greater than a set value, results in rejection of the wafer under production as being bad, in step 486. If the wafer is acceptable, the process is determined to be correct in step 487 and the cycle is repeated with a new wafer (return to step 481).

In one embodiment, the standard deviation is stored for later use in accepting or rejecting the wafer. In act 485 a decision is made as to whether another conductive structure on wafer 406 is to be evaluated. If so, acts 482–484 are repeated, e.g. until all conductive structures on wafer 406 have been evaluated. Depending on the embodiment, only selected conductive structures may be evaluated.

In act 486 the stored data are analyzed to determine if vias (which may be in the comb, serpentine or via chain) being evaluated are acceptable, or if there is a problem. If they are acceptable, the current wafer is processed further in the normal manner and a next wafer is loaded for evaluation. If they are unacceptable, the problem is reported for corrective action.

As noted above, apparatus 430 of one embodiment is a two-laser system, performing a quasi-static measurement. A red laser (830 nm wavelength) pumps heat into the metal lines in the wafer under evaluation. A second laser (980 nm wavelength) measures reflectance at the heated area to deduce temperature changes. The lasers are chosen partially for reasons of lifetime, and are rated for 100,000 hours of tool operation. As noted elsewhere herein, an external vision system, such as a Cognex PatMax vision system is used to find measurement sites in one embodiment.

Apparatus 430 of one embodiment measures metal reflectance changes due to temperature changes induced by heating with a 2 µm diameter illuminated area formed on the wafer being evaluated. The temperature rise, typically in the range of 10 to 40° C., correlates to the resistance per unit length for traces (i.e. conductive lines), and sheet resistance for pads (i.e. portions of conductive sheets). The measured signal generally increases with decreasing line cross-section area, enabling measurement of individual lines and line arrays of width <0.12 µm. As noted above, good vias shunt heat, and voids or poorly connecting interfaces between vias and underlying structures restrict heat flow, providing the measured signal with sensitivity to via continuity and line voiding.

Voids were discovered in 0.25 µm vias of a SiO2 dual damascene electrical test lot from an unrelated experiment. Specifically, the voids were found while performing FIB/SEMs of via chain structures. Three classifications of vias were observed: Fully filled, partially filled, and completely discontinuous vias. Samples from each classification of vias were also evaluated by apparatus 430 which successfully provided void measurements in via chains.

Several of the embodiments described herein do not have the drawback of reflections from trace boundaries or nearby features that occur in the prior art which is based on generation of thermal waves, because no waves are generated in these embodiments. Heating and measurement of the type described herein may be done at the same site, e.g. by using two coaxial laser beams in some embodiments. Therefore, two beams of the type described herein need not each be independently positioned relative to the geometry of the conductive structure, as may be required in some prior art. Depending on the embodiment, two beams (which may or may not be laser beams) can be positioned with a predetermined distance of separation there-between, instead of the two beams being coincident. The distance of separation may be small enough for illuminated areas formed by the two beams on a wafer to overlap, or the distance may be large enough for the illuminated areas to be completely separated from one another, depending on the implementation.

A process for making a test structure of the type described herein for some embodiments is described next. First, a photoresist layer is applied to the surface of a conductive layer formed on a substrate. Next, the photoresist layer is patterned by exposing and developing the resist in certain regions, followed by etching the exposed portion of conductive layer thereby to form openings therein. The regions of conductive layer that are protected by the photoresist remain intact and form traces or pads in the test structure.

The just-described acts (in the previous paragraph) are also used simultaneously for the creation of one or more portions of a transistor in the silicon wafer. For example, the conductive leads to/from the transistor are formed simultaneously with formation of traces/pads of the test structure, depending on the embodiment. If so, the photoresist layer is not exposed and developed at the locations of the to-be-formed regions for the transistors at the same time as regions the test structure are being formed. Alternatively, all of the regions of the various transistors in a wafer may be formed by acts separate and different from the just-described acts for formation of a test structure, again depending on the embodiment.

When integrated circuits are fabricated on wafers, they are usually formed in regions called dies. These are typically rectangular in shape and contain all the structures needed for a fully functional integrated circuit. Depending on the complexity of the circuit, the die can be as large as 2–3 cm on a side, and several tens to hundreds of dies can be on a wafer. After fabrication, the wafer is cut into individual dies with a saw. The region in between the dies reserved for this cutting operation is called the street, which is typically 50–100 µm wide.

During manufacturing of a wafer, this "street" region is used, in some embodiments of the invention, for fabrication of test structures that may be probed as part of the process flow. For example, a long via chain with dimensions 50×50 µm may be fabricated within the street adjacent to each die. Because these via chains are in close proximity to the active area of the neighboring device, they provide controlled regions that contain vias equivalent to those found in the active area. In one embodiment, these regions are probed using a method in accordance with the invention disclosed here to determine the integrity of vias. In another embodiment, vias within the active device structure are probed.

Note that in some embodiments, a number of measurements are classified into smaller groups of measurements that are close to one another (e.g. within 10% of one another), and an average of whichever group (called "baseline group") has the largest number of measurements is used as a fixed baseline to which all other measurements are compared. In one such embodiment, measurements in all other groups (i.e. groups other than the baseline group) are compared with the baseline, and whichever group has the largest difference from the baseline is deemed to identify locations of defective vias.

Numerous modifications and adaptations of the embodiments described herein will be apparent to the skilled artisan in view of the disclosure.

Depending on the embodiment, movement of a probe beam (and the heating beam if present) relative to the semiconductor wafer can be accomplished either by stage motion, or by a combination of optical and stage scanning (optical scanning in both axes is also feasible, although more complex).

In the combined approach, the probe beam (and the heating beam if present) is scanned in one axis, shown by the long horizontal arrows in FIG. 2G, and by stage motion in the other axis, shown by the short vertical arrow in FIG. 2G. Another scanning approach is to employ a ribbon heating beam, which may be 100 µm long and to scan the probing beam within the ribbon. In such an approach, stage motion provides translation in the other axis. In this embodiment, it is preferred for the ribbon to be perpendicular to the direction of the conductive lines (for example, in FIG. 2G, if the lines extend left-to-right, the ribbon extends top-to-bottom). This is because heat flow is predominantly along the metal lines, and this orientation sets up a temperature distribution along the lines.

Identification of a partially conductive via in a production wafer of the type described herein is useful e.g., when performing such measurements during wafer fabrication, so that process parameters used to fabricate a next wafer (e.g., creating the above-described vias) are changed as necessary (in a feedback loop), to generate wafers having vias of resistance within acceptable limits.

Depending on the embodiment, instead of a probe beam, a thermal imager with a microscope may be used for temperature measurement. Also, instead of using a heating beam, heat may be applied by an electron beam or other heat source, eliminating the need for a laser in certain embodiments. However, an electron beam has the drawback of requiring the conductive structure at the point of heat application to be exposed, while a laser beam can be used in the presence of a transparent dielectric covering the conductive structure.

A comb, serpentine and via chain are only exemplary of structures that can be evaluated as described herein. Other conductive structures can be evaluated in a similar manner. For example, a number of vias may connect between line segments (instead of the continuous lines illustrated in FIG. 2A–2C). Moreover, line segments may or may not be located in a periodic manner. Also, instead of via connections, such a structure may contain other connections between two co-planar lines (in a single metal layer) rather than from metal 1 to metal 2. In such case, the method may be used to detect shorts between adjacent metal lines. All of these cases would allow use of an evaluation method of the type described herein. Scans of different structures would have different baselines. However, changes in the quality of via connections change the measured signal from the baseline by a significant amount, which may be detected as described herein.

In some embodiments, structure 210 is a test structure and vias in structure 210 are spaced sufficiently apart to determine the line or pad properties independent of via properties, thereby minimizing the effect on the measurement of variation in the line or pad. In another embodiment, an additional structure of lines without vias is included in a production wafer, in addition to structure 210, and a measurement of the line (or pad) properties is made at the additional structure, and a correction for a deviation in line properties is made to the via measurement thereby to reduce or eliminate the effect of variation in the line or pad properties on the evaluation of vias.

For example, a slightly wider line has a greater thermal conductivity, and therefore a lower temperature. In the just-described example, the via measurement is normalized based on the line width measurement, thereby to ensure that line width variation is taken into account in evaluating a via chain in several embodiments of the type described above. This line width measurement may be obtained, for example, after the trench etch used to form the grooves in which the metal lines lie. In addition, more detailed measurements may determine the sidewall angle of the grooves, thereby accurately determining their cross-section.

In some structures, the lines interconnecting vias are made with large cross-section relative to the vias, so that the thermal impedance of the vias is large compared to the thermal impedance of the lines, reducing the effect of variation in the line cross-section on the via properties.

Several embodiments of the type described herein improve the throughput as compared to certain prior art. Specifically, certain prior art measurements require testing of a large number of vias to determine a failed fraction. This requires a large area of a wafer to be dedicated to a test structure. Consequently, testing of vias is not possible on production wafers, since area dedicated to test structures cannot be used for product (i.e. integrated circuit dies).

In contrast, several embodiments enable via quality to be determined by measuring a small number of vias, which in turn enables use of test structures on production wafers. Specifically, in some embodiments, a test structure 210 is built into a scribe line (area between two adjacent dies on a production wafer). Such embodiments therefore provide the basis for the use of well-known statistical process control (SPC) methods to control via quality during normal production.

Also, although in some embodiments, a measurement in a region is compared to an average of a plurality of measurements in adjacent regions, in other embodiments the measurement is compared to a predetermined value. The predetermined value is selected by correlating such measurements to known via resistances—thereby calibrating the measurement in units of via resistance such as ohms—and applying the measurement to measure via resistance itself, without necessarily comparing it to a value.

Moreover, although conductive islands of square and circular shapes have been discussed above, such islands can have other shapes, such as triangular.

Also, several embodiments involve scanning a dense via chain with a period smaller than the beam size, or scanning a flat via connected feature such as a via-connected comb or serpentine, so the baseline noise is small. Moreover, in some embodiments, the structure being scanned is a via comb over a pad (in the lower layer), which is advantageous because the connection to the pad has an enhanced probability of having a void and thus acts as a sensitive indicator of a voiding problem that may not have shown up in vias connecting to lines (in the lower layer). Such structures therefore provide higher throughput than the prior art because they yield a uniform (flat or weakly undulating) baseline signal (in case of no defects).

Numerous such modifications and adaptations of the embodiments and examples described herein are encompassed by the attached claims.

What is claimed is:

1. A method of identifying a defective location in a conductive structure formed in a semiconductor wafer, the method comprising:
   applying heat to the conductive structure at an intensity that changes over time;
   measuring electromagnetic radiation from an area of the conductive structure, as a function of changing intensity of applied heat, the area of a single measurement being sufficiently large to cover a plurality of vias;
   comparing the single measurement with a plurality of measurements obtained by performing said measuring in other areas while applying heat; and
   providing an indication about a suspected defect in said area, in response to the comparison.

2. The method of claim 1 further comprising:
   receiving said wafer with said conductive structure formed therein to comprise a first conductive layer patterned into at least one island, said island being connected to at least one via.

3. The method of claim 2, wherein:
   the conductive structure further comprises a second conductive layer that is unpatterned and forms a sheet of conductive material; and
   each via is located between the first conductive layer and the second conductive layer.

4. The method of claim 2, wherein:
   the conductive structure further comprises a second conductive layer that is patterned to form a line of conductive material; and
   each via is located between the first conductive layer and the second conductive layer.

5. The method of claim 1, wherein the conductive structure comprises a via chain.

6. The method of claim 5, wherein:
   each via is connected to at most one trace in a first conductive layer and to another trace in a second conductive layer;
   said plurality of vias are located periodically in space along a direction; and
   said area has a dimension that is several times larger than a pitch between two vias in said plurality of vias.

7. The method of claim 1 further comprising:
   receiving said wafer with said conductive structure formed therein to comprise a first conductive layer patterned into a shape selected from a group consisting of a serpentine and a comb; and
   wherein said vias are located between the first conductive layer and a second conductive layer and at least a majority of said vias form electrical connections between said first conductive layer and said second conductive layer.

8. The method of claim 7, wherein:
   the second conductive layer is also patterned into the shape selected from said group.

9. The method of claim 7, wherein:
   the second conductive layer is unpatterned and forms a continuous sheet of conductive material.

10. The method of claim 1, further comprising:
    computing a standard deviation of said plurality of measurements and computing a baseline using said standard deviation.

11. The method of claim 10, wherein:
    said baseline is an average of said plurality of measurements.

12. The method of claim 1, wherein:
    said plurality of measurements are performed at least along a direction defined by a plurality of vias located sequentially one after another in said conductive structure.

13. The method of claim 1, wherein:
    reflection of a laser beam is measured during said measuring; and
    the laser beam illuminates said area of the conductive structure.

14. The method of claim 1, wherein:
    a first beam is incident on a first trace in the conductive structure during said measuring; and
    a second beam is coincident with said first beam during said measuring, the second beam having a wavelength greater than a pitch between two vias in said conductive structure.

15. The method of claim 1, wherein:
    said measuring is performed while moving a stage carrying the semiconductor wafer containing the conductive structure; and
    said measuring is performed continuously, thereby to obtain an analog signal.

16. The method of claim 10, wherein:
    the baseline undulates across successive areas; and
    a change in said baseline at any area relative to a previous area is several times smaller than a corresponding change in said area identified as having said defect.

17. The method of claim 1 further comprising:
    illuminating said area with a beam of electromagnetic radiation of intensity varying over time such that each via in said area has a temperature in direct proportion to said intensity at any instant in time.

* * * * *